US009348056B2

(12) United States Patent
Fredrich et al.

(10) Patent No.: US 9,348,056 B2
(45) Date of Patent: May 24, 2016

(54) IMAGE-BASED DIRECT NUMERICAL SIMULATION OF PETROPHYSICAL PROPERTIES UNDER SIMULATED STRESS AND STRAIN CONDITIONS

(71) Applicant: BP Corporation North America Inc., Houston, TX (US)

(72) Inventors: Joanne Fredrich, Houston, TX (US); Nathan Lane, Katy, TX (US); Julianna Toms, Houston, TX (US)

(73) Assignee: BP Corporation North America Inc., Houston, TX (US)

( * ) Notice: Subject to any disclaimer, the term of this patent is extended or adjusted under 35 U.S.C. 154(b) by 0 days.

(21) Appl. No.: 14/453,466

(22) Filed: Aug. 6, 2014

(65) Prior Publication Data

US 2015/0043787 A1 Feb. 12, 2015

Related U.S. Application Data

(60) Provisional application No. 61/862,885, filed on Aug. 6, 2013.

(51) Int. Cl.
*G06K 9/00* (2006.01)
*G01V 8/00* (2006.01)
*G01N 33/24* (2006.01)
(Continued)

(52) U.S. Cl.
CPC .............. *G01V 8/00* (2013.01); *G01N 23/046* (2013.01); *G01N 33/24* (2013.01); *G06F 17/5018* (2013.01); *G06T 7/0079* (2013.01); *G06T 7/0081* (2013.01); *G06T 2207/10072* (2013.01); *G06T 2207/10081* (2013.01); *G06T 2207/20112* (2013.01); *G06T 2207/20148* (2013.01); *G06T 2207/30132* (2013.01)

(58) Field of Classification Search
None
See application file for complete search history.

(56) References Cited

U.S. PATENT DOCUMENTS 8,081,802 B2 12/2011 Dvorkin et al.
8,085,974 B2 12/2011 Dvorkin et al.
(Continued)

FOREIGN PATENT DOCUMENTS

WO 2011/149808 A2 12/2011
WO 2013/039416 A1 3/2013

OTHER PUBLICATIONS

Sakellariou et al., "An x-ray tomography facility for quantitative prediction of mechanical and transport properties in geological, biological and synthetic systems", Proc. Developments in X-ray Tomography IV, vol. 5535 (SPIE, 2004), pp. 473-484.
(Continued)

*Primary Examiner* — Nirav G Patel
(74) *Attorney, Agent, or Firm* — John L. Wood

(57) ABSTRACT

A testing system for performing image based direct numerical simulation to characterize petrophysical properties of a rock sample under the simulated deformation condition, for example as representative of subsurface conditions. A digital image volume corresponding to x-ray tomographic images of a rock sample is segmented into its significant elastic phases, such as pore space, clay fraction, grain contacts and mineral type, and overlaid with an unstructured finite element mesh. A simulated deformation is applied to the segmented image volume, and the resulting deformed unstructured mesh is numerically analyzed, for example by way of direct numerical simulation, to determine the desired petrophysical properties.

28 Claims, 20 Drawing Sheets

(51) Int. Cl.
*G06T 7/00* (2006.01)
*G01N 23/04* (2006.01)
*G06F 17/50* (2006.01)

(56) References Cited

U.S. PATENT DOCUMENTS

| | | | |
|---|---|---|---|
| 8,155,377 B2 | 4/2012 | Dvorkin et al. | |
| 8,170,799 B2 | 5/2012 | Dvorkin et al. | |
| 2010/0049451 A1 | 2/2010 | Lu et al. | |
| 2010/0128933 A1 | 5/2010 | Derzhi et al. | |
| 2011/0295580 A1* | 12/2011 | Sisk et al. | 703/10 |
| 2014/0044315 A1* | 2/2014 | Derzhi et al. | 382/109 |

OTHER PUBLICATIONS

International Search Report and Written Opinion of the ISA, PCT International Application PCT/US2014/049981 (Oct. 7, 2014).

Adams et al., "Seeded Region Growing", Trans. on Pattern Analysis and Machine Intelligence, vol. 16, No. 6 (IEEE, Jun. 1994), pp.641-647.

Arns et al., "Computation of linear elastic properties from microtomographic images: Methodology and agreement between theory and experiment", Geophysics, vol. 67, No. 5 (2002), pp. 1396-1405.

Arns et al., "Accurate Vp:Vs relationship for dry consolidated sandstones", Geophysical Research Letters vol. 29, No. 10.1029 (2002), pp. 44-1 through 44-4.

Knackstedt et al., "Velocity-porosity relationships, 1: Accurate velocity model for clean consolidated sandstones", Geophysics, vol. 68, No. 6 (2003), pp. 1822-34.

Makarynska et al., "Finite element modelling of the effective elastic properties of partially saturated rocks", computers and Geosciences, vol. 34 (Elsevier, 2008), pp. 647-57.

Ateshian et al., "Anisotropic hydraulic permeability under finite deformation", Journal of Biomechanical Engineering, vol. 132 (ASME, 2010), pp. 111004-1 through 111004-7.

Quintal et al., "Integrated numerical and laboratory rock physics applied to seismic characterization of reservoir rocks", the Leading Edge (2011), pp. 1360-67.

* cited by examiner

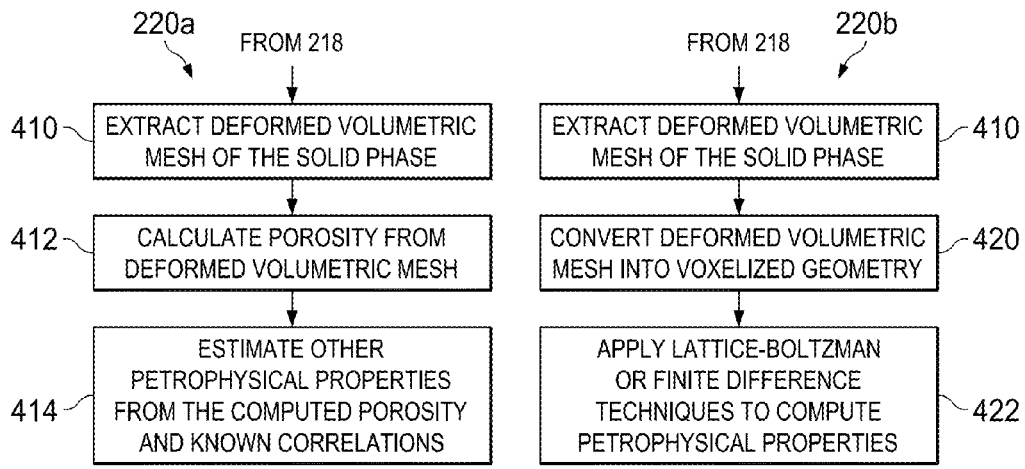
FIG. 5A
FIG. 5B
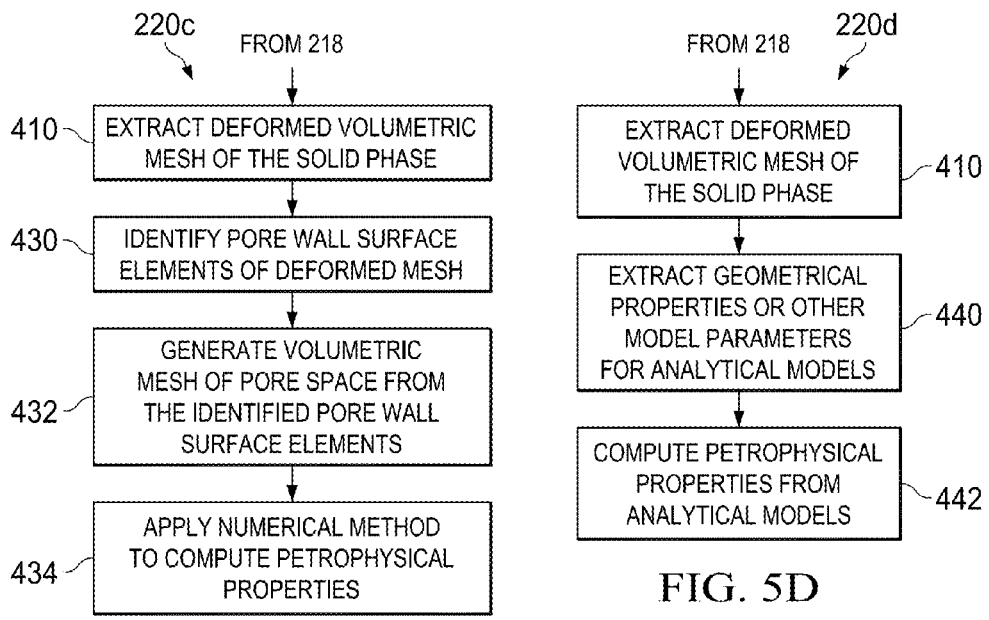
FIG. 5C
FIG. 5D

IMAGE-BASED DIRECT NUMERICAL SIMULATION OF PETROPHYSICAL PROPERTIES UNDER SIMULATED STRESS AND STRAIN CONDITIONS

CROSS-REFERENCE TO RELATED APPLICATIONS

This application claims priority, under 35 U.S.C. §119(e), of Provisional Application No. 61/862,885, filed Aug. 6, 2013, incorporated herein by this reference.

STATEMENT REGARDING FEDERALLY SPONSORED RESEARCH OR DEVELOPMENT

Not applicable.

BACKGROUND OF THE INVENTION

This disclosure relates generally to methods and systems for analyzing images of rock samples to determine petrophysical properties.

In hydrocarbon production, obtaining accurate subsurface estimates of petrophysical properties of the rock formations is important for the assessment of hydrocarbon volumes contained in the rock formations and for formulating a strategy for extracting the hydrocarbons from the rock formation. Traditionally, samples of the rock formation, such as from core samples or drilling cuttings, are subjected to physical laboratory tests to measure petrophysical properties such as permeability, porosity, formation factor, elastic moduli, and the like. As known in the art, some of these measurements require long time periods, extending over several months in some cases, depending on the nature of the rock itself. The equipment used to make these measurements can also be quite costly.

Often, petrophysical rock properties are measured in the laboratory at ambient environmental conditions, with the rock sample at room temperature and surface atmospheric pressure. However, the sub-surface environment of the rock in the formation can differ significantly from that of ambient laboratory conditions. For example, the weight of overburden sedimentation on formation rock, which increases with increasing burial depth, causes compaction of the formation rock, which is reflected in reduced porosity and permeability as compared with surface ambient conditions.

Subsurface rock formations are also subjected to changes in in situ stress/strain conditions as a result of hydrocarbon development and production. For instance, the stress conditions at a point in a rock formation adjacent to a drilled borehole will differ from the original in situ stress conditions at that same point prior to drilling. In addition, the injection and extraction of pore fluids, as occurs in field production, sets up changes in pore fluid pressure from that prior to production, which also causes changes in in situ stress conditions. Different stress or strain conditions from these and other causes can significantly alter the petrophysical properties of rock relative to the same rock under ambient conditions. Of course, it is the subsurface petrophysical properties of the rock under its in situ stress conditions that are of most interest for purposes of appraisal, development, and production of the field.

To compensate for the effect of changes in in situ stress, conventional laboratory measurements of porosity, permeability, electrical conductivity, and other petrophysical properties can be physically measured in the laboratory under a variety of stress and strain conditions. It has been observed, however, that the equipment and technician time required to artificially apply these physical conditions in the laboratory can be prohibitively expensive, as compared with tests performed under room ambient conditions, and can also require significantly more time to carry out, especially for complicated rock types. Moreover, the range of laboratory-applied stress and strain conditions for the measurement of a particular petrophysical property is often quite limited, and may not accurately represent the in situ subsurface conditions.

Even if equipment for measuring rock properties under confining stresses and pressures is available, the estimation of petrophysical properties of a given rock sample under several different stress/strain conditions is often not possible, because the microstructure of the rock sample may be permanently deformed by one or more of the loading and unloading stress/strain cycles. This deformation may occur, for instance, when measuring petrophysical properties of a given rock sample initially under hydrostatic stress conditions (i.e., where the sample is subjected to uniform confining pressure) and then measuring the petrophysical properties of the same rock under uniaxial stress conditions (i.e., where stress is applied in only a single direction, with no applied stress in all other directions). In that case, subsequent iterations of the measurement experiment on the same sample can result in a different petrophysical property value or other change in physical behavior that is not representative of the true stress/strain response of the rock. The measured petrophysical properties in the second and subsequent stress experiments may thus differ significantly from the true in situ values sought for those stress experiments.

Because of the cost and time required to directly measure petrophysical properties, the technique of "direct numerical simulation" has been developed for efficiently estimating physical properties, such as porosity, absolute permeability, relative permeability, formation factor, elastic moduli, and the like of rock samples, including samples from difficult rock types such as tight gas sands or carbonates. According to this approach, a three-dimensional tomographic image of the rock sample is obtained, for example by way of a computer tomographic (CT) scan. Voxels in the three-dimensional image volume are "segmented" (e.g., by "thresholding" their brightness values or by another approach) to distinguish rock matrix from void space. Numerical simulation of fluid flow or other physical behavior such as elasticity or electrical conductivity is then performed, from which porosity, permeability (absolute and/or relative), elastic properties, electrical properties, and the like can be derived. A variety of numerical methods may be applied to solve or approximate the physical equations simulating the appropriate behavior. These methods include the Lattice-Boltzmann, finite element, finite difference, finite volume numerical methods and the like.

However, conventional direct numerical simulation is generally limited to rock samples under ambient stress/strain conditions, in that images obtained by X-ray tomographic images or other imaging techniques (e.g., FIBSEM) are generally acquired under ambient conditions. This is because the mechanical equipment required to induce stress/strain conditions are not routinely attached to imaging equipment, or cannot feasibly be so attached, due to the nature of either or both of the imaging and mechanical devices. In those cases in which imaging and mechanical testing have been combined, such as by using special sample holders that are transparent to X-ray tomography, such combined experimental apparatus is highly specialized and extremely expensive, and may involve health and safety risks.

BRIEF SUMMARY OF THE INVENTION

Embodiments of this invention provide a system and method for simulating the subsurface conditions found in rock formations in the direct numerical simulation of physical processes from which petrophysical properties are derived.

Embodiments of this invention provide such a system and method that substantially reduce the time and cost of traditional laboratory tests while improving the accuracy of those tests.

Embodiments of this invention provide such a system and method that can be implemented into conventional test and analysis equipment.

Other objects and advantages of embodiments of this invention will be apparent to those of ordinary skill in the art having reference to the following specification together with its drawings.

Embodiments of this invention may be implemented into an analysis method, system, and computer-readable medium storing executable program instructions for performing such analysis, based on a three-dimensional (3D) image of a rock sample, in which voxels or other portions of the 3D image corresponding to solid material in the rock sample are differentiated from voxels or other portions of the image corresponding to pores in that rock sample. An unstructured mesh overlaid onto the regions of the image corresponding to the solid material, followed by the numerical application of a simulated deformation, in the nature of stress, strain, force, displacement, or the like, to that unstructured mesh, for example by way of boundary conditions for a finite element system of equations. The simulated deformation can represent the subsurface environment of the rock sample at its original location in the formation. The effects of the simulated deformation, as represented by changes in the unstructured mesh, are intended to emulate deformations in the rock sample at the stress or strain levels in the sub-surface. At least one petrophysical property of the rock sample is then numerically or analytically determined for the unstructured mesh, as deformed by the simulated deformation.

BRIEF DESCRIPTION OF THE SEVERAL VIEWS OF THE DRAWING

FIGS. 5A through 5D are flow diagrams illustrating the method of FIG. 2 according to each of several embodiments of the invention.

DETAILED DESCRIPTION OF THE INVENTION

Figure 1A:
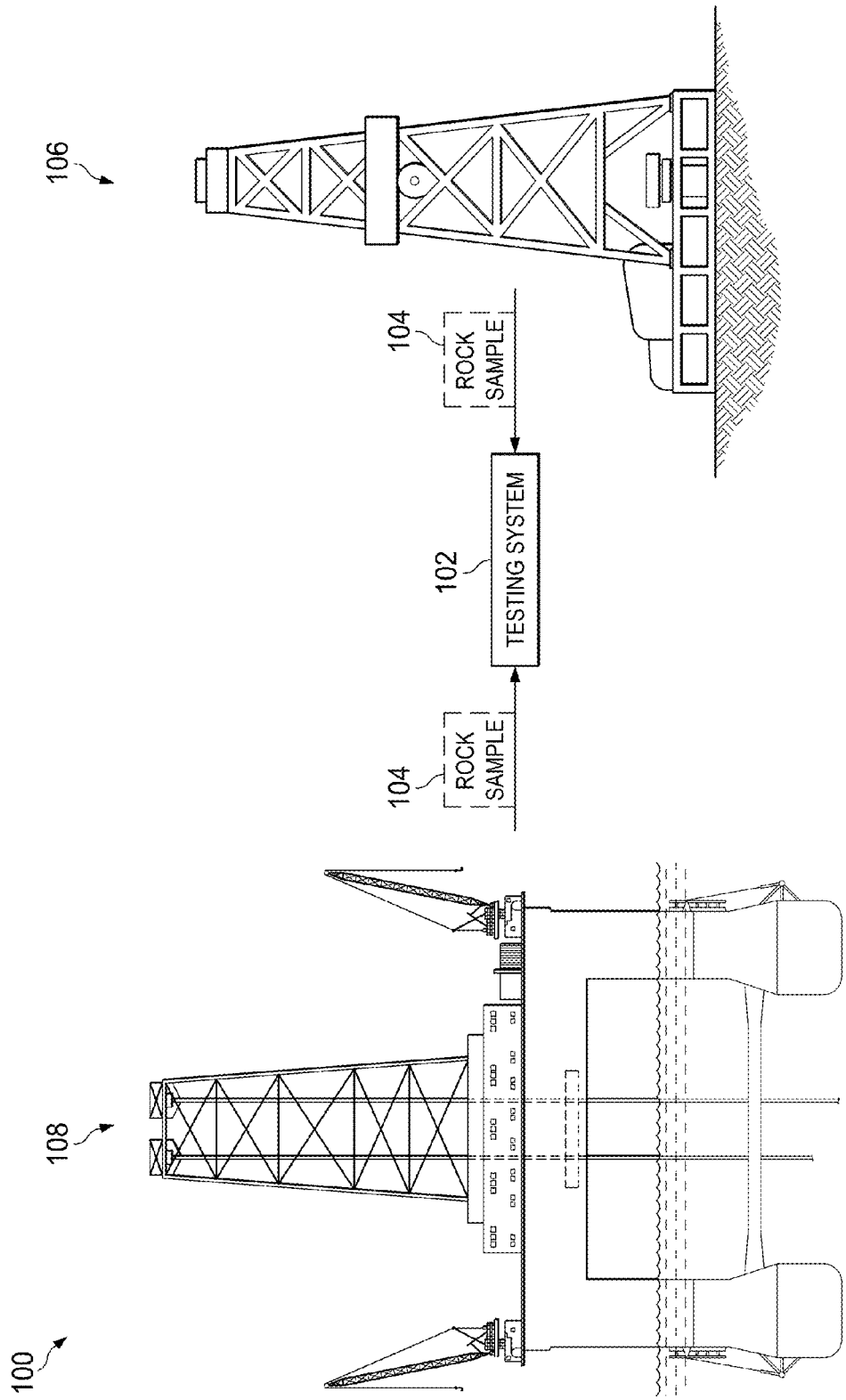
FIG. 1A is a generic block diagram that illustrates examples of sources of rock samples for a testing system constructed and operating according to embodiments of the invention.

This invention will be described in connection with its embodiments, namely as implemented into methods, systems, and corresponding software for analyzing samples of sub-surface formations by way of direct numerical simulation, with stress and strains numerically applied to those samples to investigate sub-surface effects of in situ stress and other conditions, as it is contemplated that this invention will be particularly beneficial when utilized for such results. However, it is contemplated that the invention can be beneficially applied to other applications, for example to replicate mechanical laboratory testing, and to determine other physical properties beyond those described in this specification. Accordingly, it is to be understood that the following description is provided by way of example only, and is not intended to limit the true scope of this invention as claimed.

Embodiments of this invention are directed to systems and methods for numerical simulation of petrophysical properties under simulated stress/strain arising from the numerical application of stress, strain, force, or displacement boundary conditions and the numerical solution of appropriate constitutive equations for elasticity, which relate material stresses, strains, and other properties. More specifically, a testing system performs an image based direct numerical simulation of the petrophysical properties of a sample of rock, where the deformation is a result of the numerical application of stress, strain, force, or displacement boundary conditions and the numerical solution of the appropriate constitutive equations. Moreover, the application of specific stress, strain, force, or displacement boundary conditions may represent one or more subsurface conditions, such as the in situ stress conditions experienced by the rock in its original subsurface location. Other boundary conditions beyond stress, strain, force, and displacement, such as those involving rotations, rate-dependent displacements or strains, and the like, as well as those formulations that can be utilized to solve problems involving plasticity and other non-linearities, among others, may alternatively be used in connection with the disclosed embodiments, and are contemplated to be within the scope of the claims.

While certain embodiments will be described in this specification with reference to analysis of the effects of subsurface stress/strain conditions on the petrophysical properties of rock, it is contemplated that these embodiments can also be utilized to explore the general effect of different stress/strain paths on the petrophysical properties of rock, even though such paths may or may not correspond directly to subsurface stress/strain conditions or to the evolution of subsurface stress/strain conditions. In particular, according to some embodiments, gradual or incremental increases in stress or strain may be numerically applied, with petrophysical properties simulated at each incremental step. These stress/strain conditions may stand in direct analogy to traditional laboratory experiments designed to test the mechanical properties of rock, such experiments including hydrostatic tests, uniaxial compression, uniaxial strain, triaxial tests, and the like.

FIG. 1A illustrates, at a high level, the acquiring of rock samples and their analysis according to embodiments of this method. It is contemplated that embodiments of this invention will be especially beneficial in analyzing rock samples from sub-surface formations that are important in the production of oil and gas. As such, FIG. 1A illustrates environments 100 from which rock samples 104 to be analyzed by testing system 102 can be obtained, according to various implementations. In these illustrated examples, rock samples 104 can be obtained from terrestrial drilling system 106 or from marine (ocean, sea, lake, etc.) drilling system 108, either of which is utilized to extract resources such as hydrocarbons (oil, natural gas, etc.), water, and the like. As is fundamental in the art, optimization of oil and gas production operations is largely influenced by the structure and physical properties of the rock formations into which terrestrial drilling system 106 or marine drilling system 108 is drilling or has drilled in the past.

It is contemplated, in embodiments of this invention, that the manner in which rock samples 104 are obtained, and the physical form of those samples, can vary widely. Examples of rock samples 104 useful in connection with embodiments of this invention include whole core samples, side wall core samples, outcrop samples, drill cuttings, and laboratory generated synthetic rock samples such as sand packs and cemented packs.

Figure 1B:
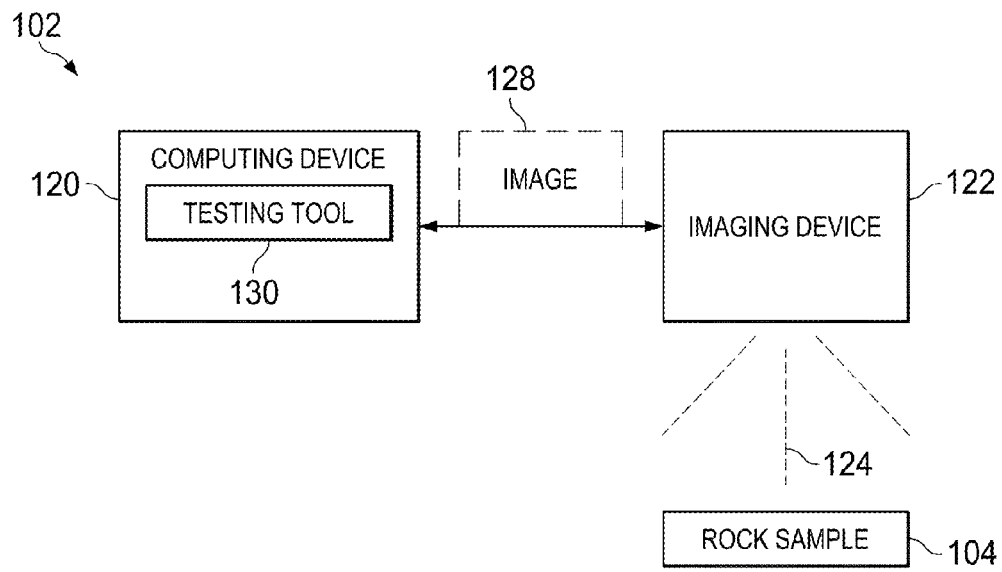
FIG. 1B is an electrical diagram, in block form, of a testing system for analyzing rock samples according to embodiments of the invention.

As illustrated in FIG. 1A, environment 100 includes testing system 102 that is configured to analyze images 128 of rock samples 104 in order to determine the physical properties of the corresponding sub-surface rock, such properties including petrophysical properties in the context of oil and gas exploration and production. FIG. 1B illustrates, in a generic fashion, the constituent components of testing system 102 in performing such analysis.

In a general sense, testing system 102 includes imaging device 122 for obtaining two-dimensional (2D) or three-dimensional (3D) images, as well as other representations, of rock samples 104, such images and representations including details of the internal structure of those rock samples 104. An example of imaging device 122 is a X-ray computed tomography (CT) scanner, which as known in the art emits x-ray radiation 124 that interacts with an object and measures the attenuation of that x-ray radiation 124 by the object in order to generate an image of its interior structure and constituents. The particular type, construction, or other attributes of CT scanner 122 can correspond to that of any type of x-ray device, such as a micro CT scanner, capable of producing an image representative of the internal structure of rock sample 104. In this example, imaging device 122 generates one or more images 128 of rock sample 104, and forwards those images 128 to computing device 120.

The form of images 128 produced by imaging device 122 in this example may be in the form of a three-dimensional (3D) digital image volume consisting of or generated from a plurality of two-dimensional (2D) sections of rock sample 104. In this case, each image volume is partitioned into 3D regular elements called volume elements, or more commonly "voxels". In general, each voxel is cubic, having a side of equal length in the x, y, and z directions. Digital image volume 128 itself, on the other hand, may contain different numbers of voxels in the x, y, and z directions. Each voxel within a digital volume has an associated numeric value, or amplitude, that represents the relative material properties of the imaged sample at that location of the medium represented by the digital volume. The range of these numeric values, commonly known as the grayscale range, depends on the type of digital volume, the granularity of the values (e.g., 8 bit or 16 bit values), and the like. For example, 16 bit data values enable the voxels of an x-ray tomographic image volume to have amplitudes ranging from 0 to 65,536 with a granularity of 1.

As mentioned above, imaging device 122 forwards images 128 to computing device 120, which in the example of FIG. 1B may be any type of conventional computing device, for example, a desktop computer or workstation, a laptop computer, a server computer, a tablet computer, and the like, and as such computing device 120 will include hardware and software components typically found in a conventional computing device. As shown in FIG. 1B, these hardware and software components of computing device 120 include testing tool 130 that is configured to analyze images 128 to determine the petrophysical properties of rock sample 104 under one or more simulated deformation conditions, including stress and strain conditions that may be encountered by rock formations in the sub-surface. In this regard, testing tool 130 may be implemented as software, hardware, or a combination of both, including the necessary and useful logic, instructions, routines, and algorithms for performing the functionality and processes described in further detail below. In a general sense, testing tool 130 is configured to analyze image volume 128 of rock sample 104 to perform numerical simulation of the petrophysical properties under the simulated deformation representing subsurface conditions of rock formations.

Figure 1C:
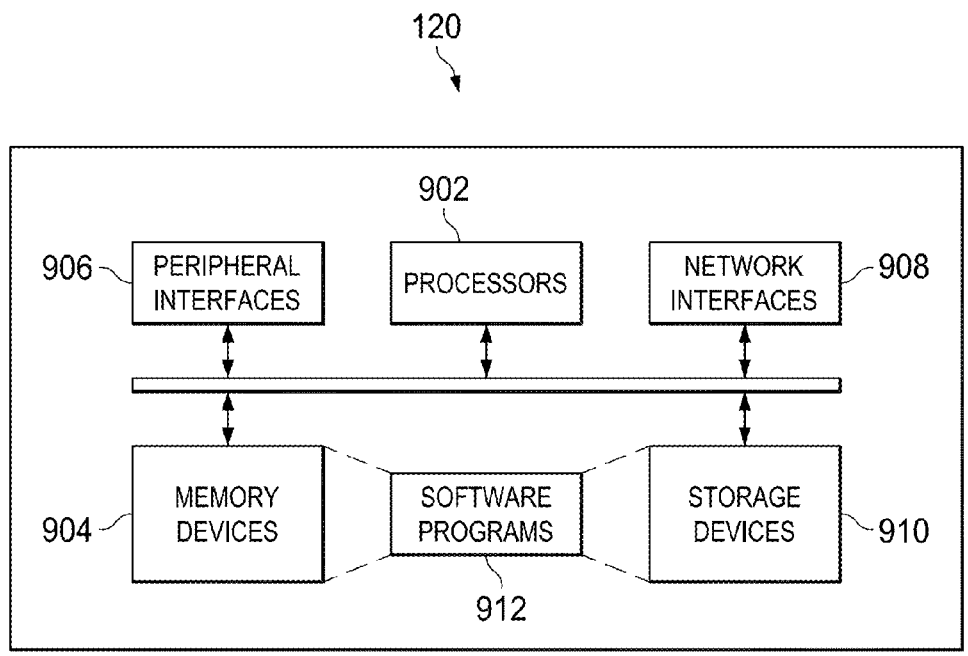
FIG. 1C is an electrical diagram, in block form, of the construction of a computing device in the system of FIG. 1B, according to embodiments of the invention.

FIG. 1C generically illustrates the architecture of computing device 120 in testing system 102 according to embodiments of the invention. In this example architecture, computing device 120 includes one or more processors 902, which may be of varying core configurations and clock frequencies as available in the industry. The memory resources of computing device 120 for storing data and also program instructions for execution by the one or more processors 902 include one or more memory devices 904 serving as a main memory during the operation of computing device 120, and one or more storage devices 910, for example realized as one or more of non-volatile solid-state memory, magnetic or optical disk drives, random access memory. One or more peripheral interfaces 906 are provided for coupling to corresponding peripheral devices such as displays, keyboards, mice, touchpads, touchscreens, printers, and the like. Network interfaces 908, which may be in the form of Ethernet adapters, wireless transceivers, or serial network components, are provided to facilitate communication between computing device 120 via one or more networks such as Ethernet, wireless Ethernet, Global System for Mobile Communications (GSM), Enhanced Data rates for GSM Evolution (EDGE), Universal Mobile Telecommunications System (UMTS), Worldwide Interoperability for Microwave Access (WiMAX), Long Term Evolution (LTE), and the like. In this architecture, processors 902 are shown as coupled to components 904, 906, 908, 910 by way of a single bus; of course, a different interconnection architecture such as multiple, dedicated, buses and the like may be incorporated within computing device 120.

While illustrated as a single computing device, computing device 120 can include several computing devices cooperating together to provide the functionality of a computing device. Likewise, while illustrated as a physical device, computing device 120 can also represent abstract computing devices such as virtual machines and "cloud" computing devices.

As shown in the example implementation of FIG. 1C, computing device 120 includes software programs 912 including one or more operating systems, one or more application programs, and the like. According to embodiments of the invention, software programs 912 include program instructions corresponding to testing tool 130 (FIG. 1B), implemented as a standalone application program, as a program module that is part of another application or program, as the appropriate plug-ins or other software components for accessing testing tool software on a remote computer networked with computing device 120 via network interfaces 908, or in other forms and combinations of the same.

The program memory storing the executable instructions of software programs 912 corresponding to the functions of testing tool 130 may physically reside within computing device 120 or at other computing resources accessible to computing device 120, i.e. within the local memory resources of memory devices 904 and storage devices 910, or within a server or other network-accessible memory resources, or distributed among multiple locations. In any case, this program memory constitutes computer-readable medium that stores executable computer program instructions, according to which the operations described in this specification are carried out by computing device 120, or by a server or other computer coupled to computing device 120 via network interfaces 908 (e.g., in the form of an interactive application upon input data communicated from computing device 120, for display or output by peripherals coupled to computing device 120). The computer-executable software instructions corresponding to software programs 912 associated with testing tool 130 may have originally been stored on a removable or other non-volatile computer-readable storage medium (e.g., a DVD disk, flash memory, or the like), or downloadable as encoded information on an electromagnetic carrier signal, in the form of a software package from which the computer-executable software instructions were installed by computing device 120 in the conventional manner for software installation. It is contemplated that those skilled in the art will be readily able to implement the storage and retrieval of the applicable data, program instructions, and other information useful in connection with this embodiment of the invention, in a suitable manner for each particular application, without undue experimentation.

The particular computer instructions constituting software programs 912 associated with testing tool 130 may be in the form of one or more executable programs, or in the form of source code or higher-level code from which one or more executable programs are derived, assembled, interpreted or compiled. Any one of a number of computer languages or protocols may be used, depending on the manner in which the desired operations are to be carried out. For example, these computer instructions for creating the model according to embodiments of this invention may be written in a conventional high level language such as JAVA, FORTRAN, or C++, either as a conventional linear computer program or arranged for execution in an object-oriented manner. These instructions may also be embedded within a higher-level application. In any case, it is contemplated that those skilled in the art having reference to this description will be readily able to realize, without undue experimentation, embodiments of the invention in a suitable manner for the desired installations.

The particular functions of testing tool 130, including those implemented by way of software programs 912, to analyze rock samples under simulated stress and strain conditions according to embodiments of the invention, will now be described with reference to the flow diagram of FIG. 2 in combination with FIGS. 1A through 1C.

In process 204, testing system 102 acquires rock sample 104 to be analyzed, such as from a sub-surface rock formation obtained via terrestrial drilling system 106 or marine drilling system 108, or from other sources. Process 204 typically prepares the specific rock sample 104 from a larger volume of the sub-surface rock formation, to be of a size, dimension, and configuration that may be imaged by imaging device 122 (e.g., a CT scanner), for example by drilling or cutting out a portion of the larger volume of the rock formation of interest.

According to an embodiment of the invention, imaging device 122 in combination with computing device 120 of testing system 102 generates digital image volume 128 representative of rock sample 104, including its interior structure, in process 208. For the example in which imaging device 122 is a CT scanner, process 208 is carried out by x-ray imaging of rock sample 104 (i.e., emitting radiation directed at rock sample 104 and measuring the attenuation) to generate image volumes 128 of or from 2D slice images. Specific conventional techniques for acquiring and processing 3D digital image volumes 128 of rock sample 104 in process 208 include, without limitation, X-ray tomography, X-ray micro-tomography, X-ray nano-tomography, Focused Ion Beam Scanning Electron Microscopy, and Nuclear Magnetic Resonance.

Figure 3A:
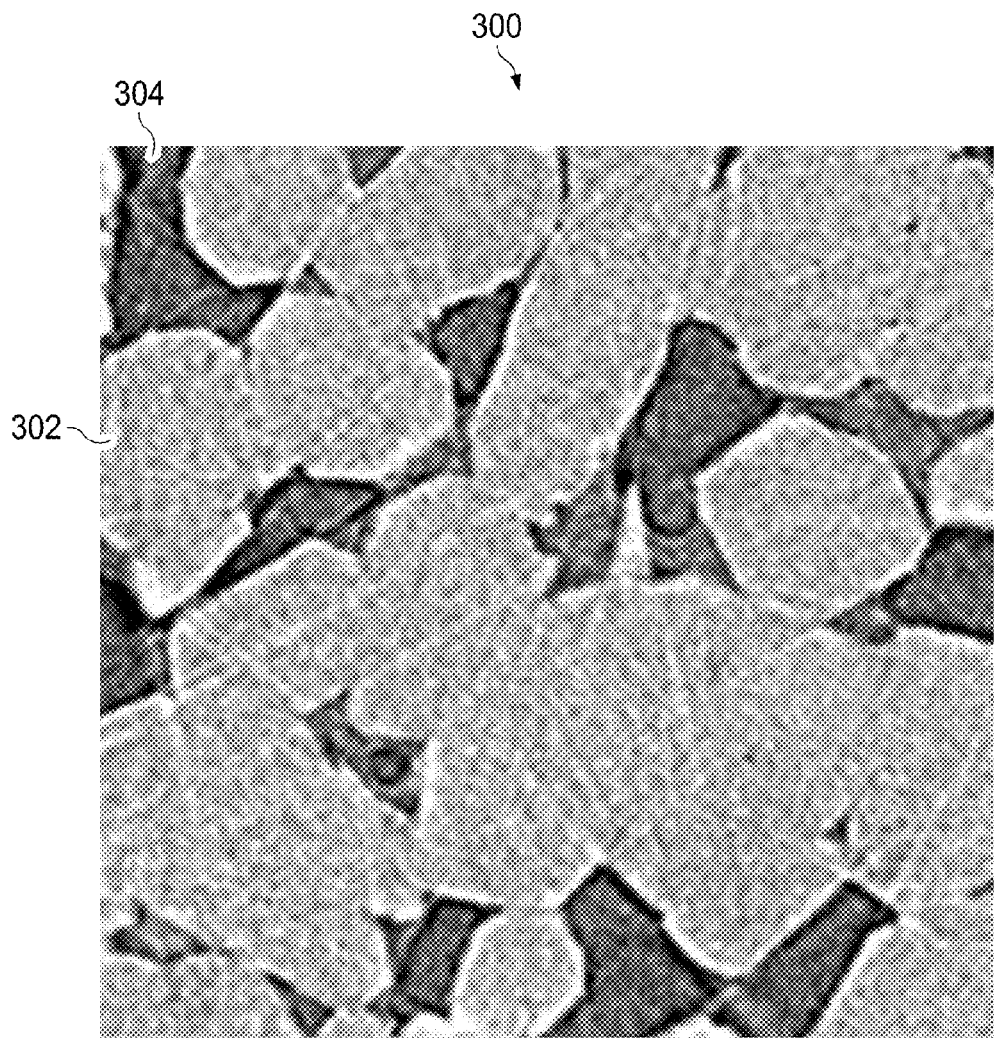
FIG. 3A is a cross-sectional microphotograph of a rock sample to which embodiments of the invention may be applied.

FIG. 3A illustrates an example of one 2D slice image 300 of a 3D image of a rock sample, which shows a cross-sectional slice of the structural details of that rock sample, including the features of solid material 302 and pores or void space 304. The image data at this point may be in the form of grayscale values representative of the attenuation of the x-ray radiation by the constituents of rock sample 104. While FIG. 3A illustrates one 2D slice image 300, 3D digital image volume 128 of rock sample 104 is typically composed of multiple 2D slice images at locations stepped along one axis of rock sample 104, together forming a 3D image of rock sample 104. The combining of the 2D slice images into 3D digital image volume 128 may be performed by computational resources within imaging device 122 itself, or by computing device 120 from the series of 2D slice images 128 produced by imaging device 122, depending on the particular architecture of testing system 102.

In process 210, testing system 102 performs segmentation or other image enhancement techniques on digital image volume 128 of rock sample 104 to distinguish and label different components of image volume 128 from the grayscale values of the image. More specifically, computing device 120 performs this segmentation in order to identify the significant elastic components, such as pore space and mineralogical components (e.g., clays and quartz), that can affect the elastic characteristics of rock sample 104, such as its stress-strain response. In some embodiments, testing tool 130 is configured to segment image volume 128 into more than two significant elastic phases, representing such material constituents as pore space, clay fraction, quartz fraction, and other various mineral types.

Figure 3B:
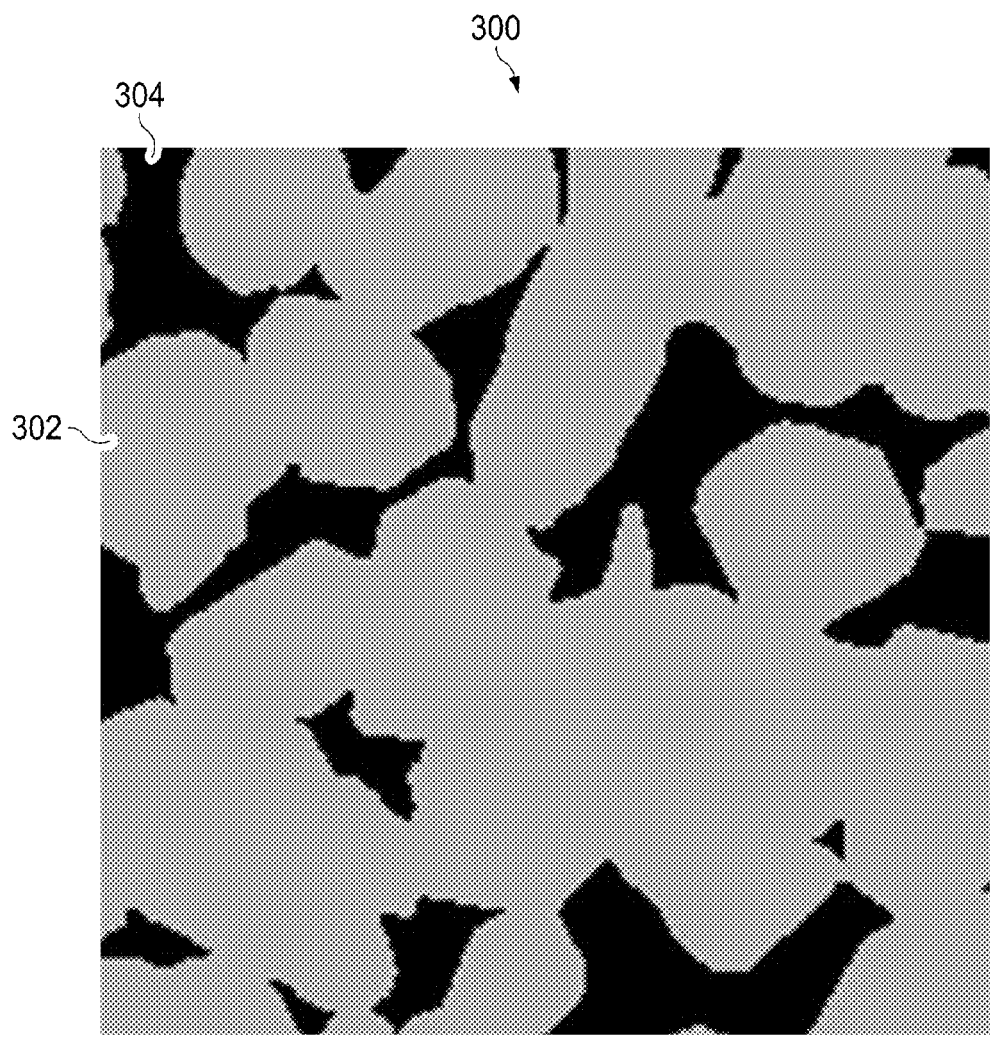
FIG. 3B through 3D are digital representations of the rock sample of FIG. 3A, to which embodiments of the invention may be applied.

To accomplish process 210, computing device 120 can utilize any one of a number of types of segmentation algorithms. One approach to segmentation process 210 is the application of a "thresholding" process to image volume 128, in which computing device 120 chooses a threshold value within the voxel amplitude range. Those voxels having an amplitude below the threshold value are assigned one specific numeric value that denotes pore space, while those voxels having an amplitude above the threshold are assigned another numeric value that denotes matrix space (i.e., solid material). In this approach, thresholding process 210 will convert a grayscale image volume to a segmented volume of voxels having one of two possible numeric values, commonly selected to be 0 and 1. FIG. 3B illustrates an example of the segmentation performed on a 3D digital image volume in thresholding process 210. As illustrated, segmentation allows the structural details of a rock sample to be distinguished, in this example with the solid material 302 shown in light gray, and pores or void space 304 shown in black. Further segmentation can be applied one or more times to differentiate various features within a grayscale image. If simple thresholding is used, multiple threshold values can distinguish among different materials exhibiting different x-ray attenuation characteristics, such as clay, quartz, feldspar, etc.

Computing device 120 may alternatively utilize other segmentation algorithms in process 120. An example of such an alternative algorithm is known in the art as Otsu's Method, in which a histogram based thresholding technique selects a threshold to minimize the combined variance of the lobes of a bimodal distribution of grayscale values (i.e., the "intraclass variance"). Otsu's method can be readily automated, and may also be extended to repeatedly threshold the image multiple times to distinguish additional material components such as quartz, clay, and feldspar. Other examples of automated segmentation algorithms of varying complexity may alternatively or additionally be used by computing device 120 to distinguish different features of an image volume, such algorithms including Indicator Kriging, Converging Active Contours, Watershedding, and the like.

As part of process 210, computing device 120 may also utilize other image enhancement techniques to enhance or improve the structure defined in image volume 128 to further differentiate among structure, to reduce noise effects, and the like. Likewise, while computing device 120 can perform the segmentation or other image enhancement techniques in process 210, it is contemplated that other components of testing system 102, for example imaging device 122 itself, may alternatively perform image enhancement process 210 in whole or in part.

Also in process 210, computing device 120 may formulate an assignment volume from the segmented image volume 128, within which appropriate elastic parameters are assigned to each distinct elastic phase. According to embodiments of the invention, and as will be described in detail below, testing tool 130 will apply boundary conditions on a meshed version of this assignment volume to represent the desired in situ deformation under which the constitutive governing equations appropriate for linear elasticity, viscoelasticity, plasticity, or other physical laws are to be solved to simulate the appropriate physical response of the rock volume to the deformation.

Figure 3C:
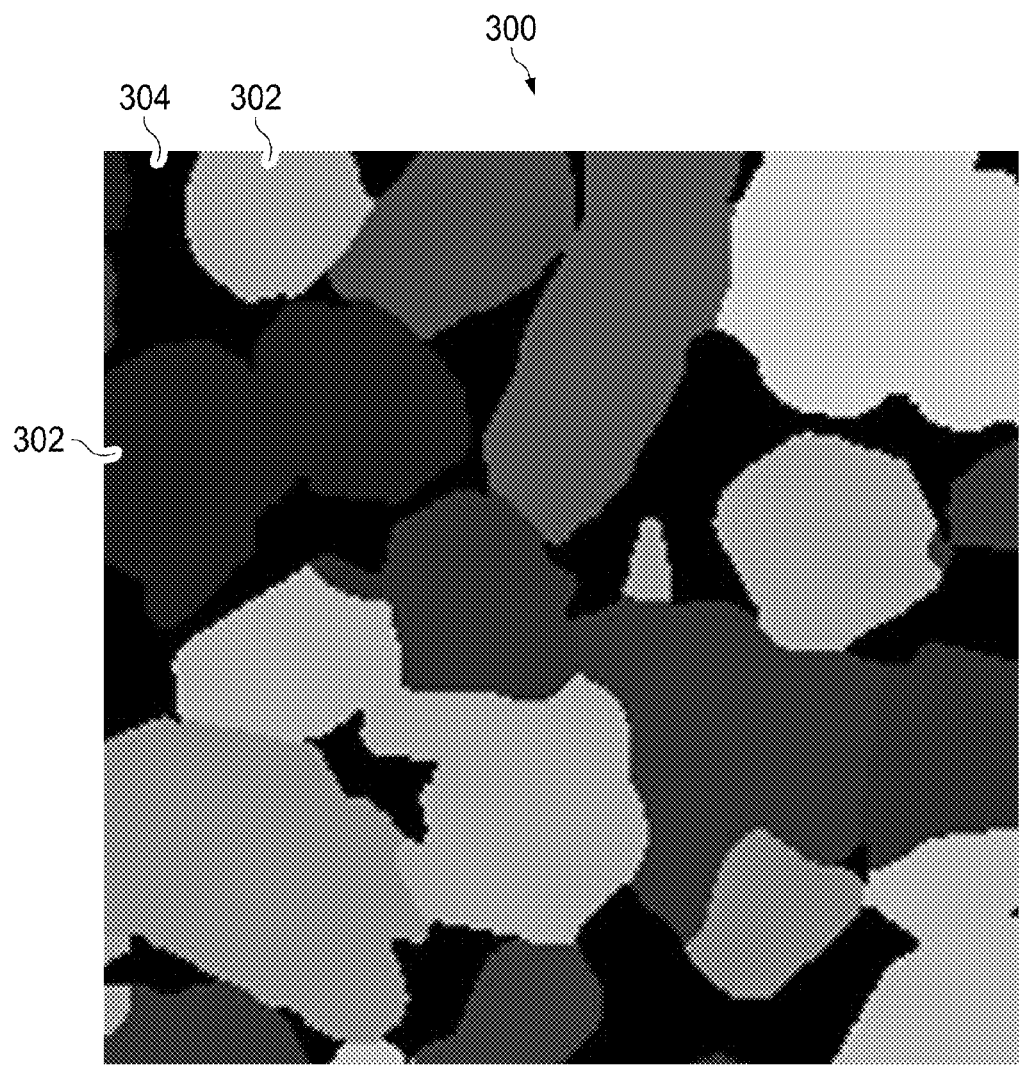
Figure 3D:
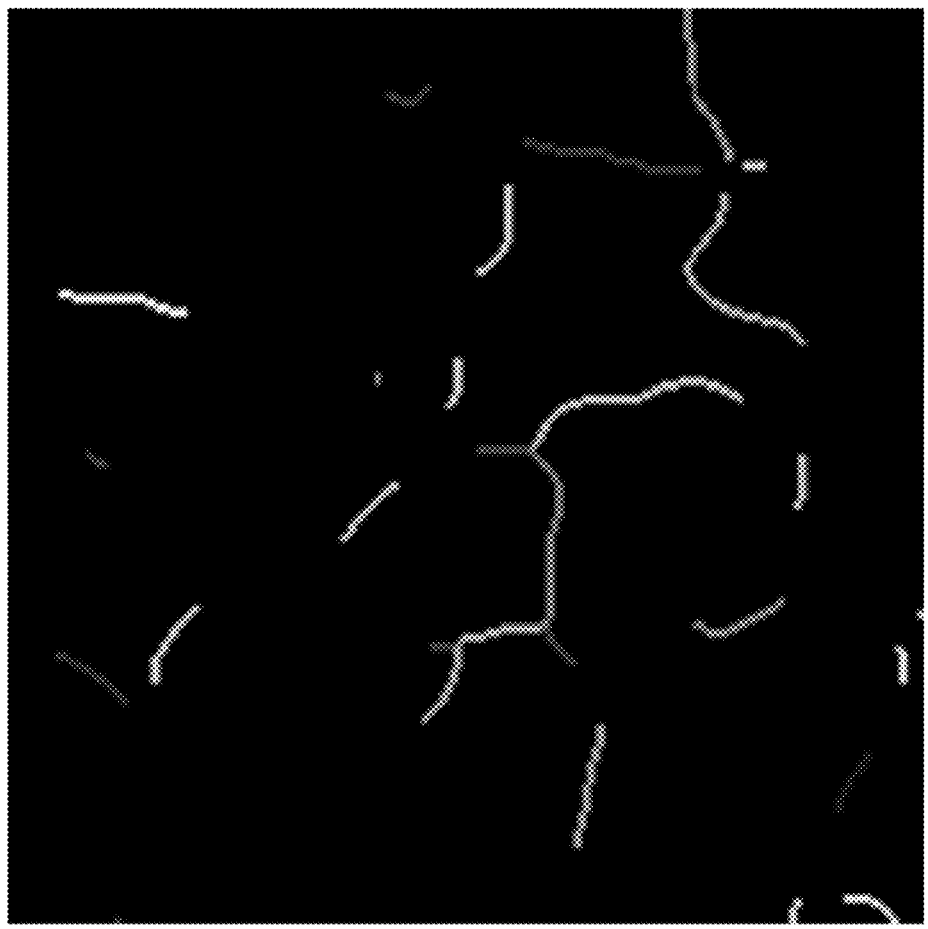

Process 212 is an optional process by way of which testing system 102 performs grain partitioning and grain contact identification to identify the separate grains and contact regions between each grain of rock sample 104 as represented by image volume 128. Contact regions correspond to those portions of the surfaces of individual grains that are in contact with other grains. In some embodiments of the invention, analysis of the contact regions between grains and their characteristics, such as degree of cement, rugosity, etc., is useful as these contact characteristics can have an effect on the stress-strain response of the rock. FIGS. 3C and 3D illustrate examples of the grain partitioning and grain contact identification performed on the segmented 2D slice image 300 of FIG. 3B, in an instance of optional process 212. As illustrated in FIG. 3C, each unique grain in the 2D slice image is randomly shaded to a different grayscale value to distinguish the grains from one another. The particular grayscale value to which each individual grain is shaded reflects a unique numeric label utilized to identify an individual grain in the solid matrix. As illustrated in FIG. 3D, the grain to grain contacts for each unique grain are highlighted with a different grayscale value from the body of their respective grains, as a result of optional process 212.

Process 210 (including optional process 212 if performed) thus associates the voxels in the segmented digital image volume with the particular material (or pore space, as the case may be) at the corresponding location within rock sample 104. In process 210 (and optional process 212 if performed), some or all of the voxels are each labeled with one or more material properties corresponding to the particular material constituent assigned to that voxel by processes 210, 212, such constituents including pore space, matrix material, clay fraction, individual grains, grain contacts, mineral types, and the like. The particular elastic or other material properties of those identified constituents are associated with corresponding voxels to the extent useful for the analysis to be performed, i.e. grains and minerals within the volume are assigned appropriate densities and elastic properties.

For instance, when individual grains, minerals, and contacts are assumed to behave according to linear elasticity, it is useful to assign values for Young's modulus E and Poisson's ratio v to each voxel that is labelled as an individual grain, mineral, or contact. As known in the art, Young's modulus is a measure of the stiffness of a material undergoing uniaxial stress deformation that is linear (i.e., the relationship of stress as a function of strain is linear, with a slope equal to the value of Young's modulus E). Also as known in the art, Poisson's ratio is a measure of the lateral and longitudinal strain under conditions of uniaxial stress behavior. Alternatively, values for bulk modulus K and shear modulus G may be assigned to grains, minerals, and contacts in the material to describe the elastic behavior of those components. As known in the art, bulk modulus is a measure of the elastic response of a material to hydrostatic pressure, while shear modulus is a measure of the elastic response of a material to shear strains. As known in the art, all of these elastic coefficients are interrelated with one another by way of well-known transforms. It is contemplated that, for those cases in which linear elastic materials are concerned, Young's modulus and Poisson's ratio will typically be ascribed to components of the material because values for these parameters can be determined directly through experiments.

In circumstances where minerals, grains, or contacts are assumed to exhibit viscoelastic behavior, such that the deformation in response to an applied stress or strain is rate dependent, it is necessary to assign appropriate model parameters, like stiffness and viscosity, if for example Maxwell materials are assumed. There are a multitude of other constitutive models known in the art that are appropriate for viscoelastic and plastic materials, and which may be utilized to describe various types of stress/strain behavior. In any case, the model parameters assigned to the materials should be those appropriate for the specific constitutive model that is assumed.

Process 214 is then executed by testing system 102 to generate a finite element mesh for the solid material (or for the partitioned identified grains and contact regions from process 212) in the segmented 3D image volume of rock sample 104. In embodiments of this invention, computing device 120 executes testing tool 130 to create this finite element mesh as an unstructured mesh applied to the segmented 3D image volume. This finite element mesh is "unstructured" in the sense that it consists of a number of polygonal elements in an irregular pattern (i.e., with irregular connectivity), in contrast to a "structured" mesh of polygonal elements in a regular pattern (i.e., with regular connectivity). In embodiments of this invention in which grain contacts are identified in optional process 212, the unstructured mesh can be refined (i.e., more finely patterned) in and near the identified contact regions. Computing device 120 then assigns the material properties of each labeled component of each voxel to corresponding elements of the unstructured mesh, also in process 214.

Figure 3E:
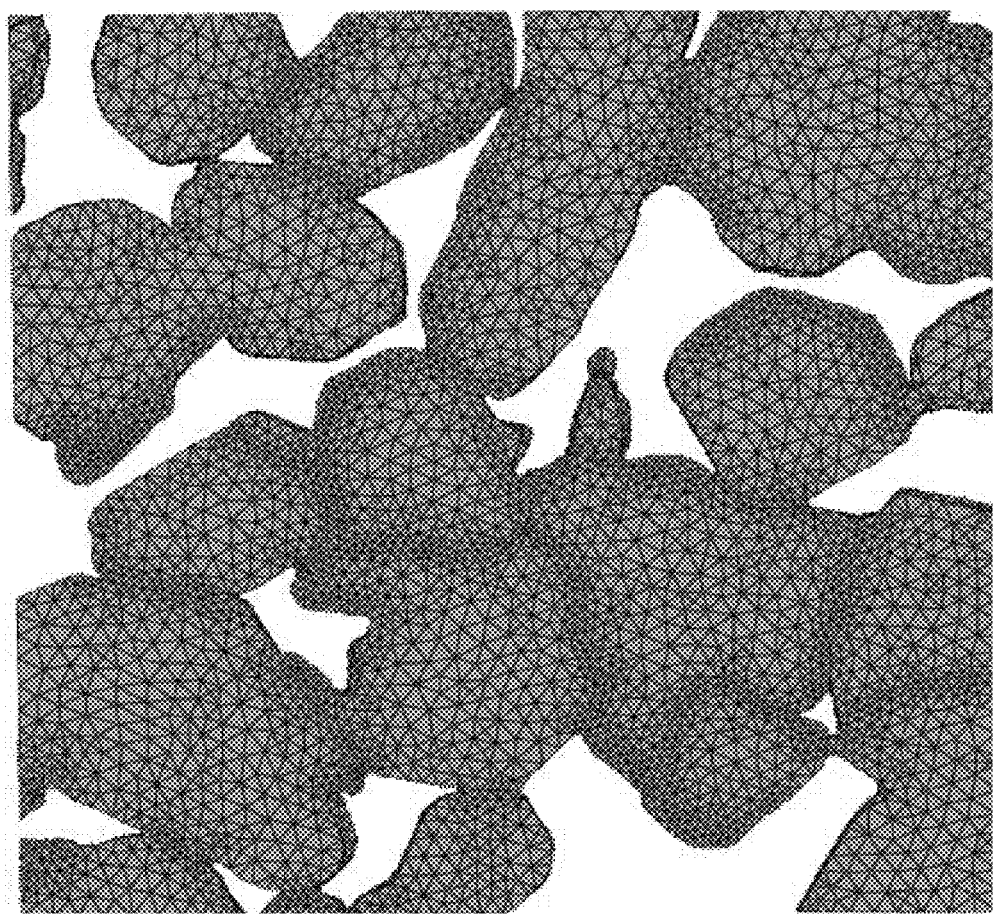
FIG. 3E is a digital plot illustrating an unstructured mesh as applied to a digital representation of a rock sample, before deformation.

FIG. 3E illustrates an example of an unstructured mesh as created in process 214 from a 3D segmented image volume generated in processes 210, 212. The view shown in FIG. 3E is a 2D representation of a 3D unstructured mesh, in which the portions of the image slice representing solid material 302 are represented by finite elements that are of differing size and connectivity from one another. Each of these finite elements are also assigned the material properties corresponding to the labeled component (e.g., solid material 302 generally, or the particular material represented) that it overlays. While FIG. 3E illustrates a single 2D slice image 300 and the cross-sections (shown as triangles) of each finite element in that view, the finite elements of the unstructured mesh are considered as three-dimensional (tetrahedral) elements that have been applied to 3D digital image volume 128 composed of a series of such 2D slice images. While FIG. 3E illustrates mesh generation using tetrahedral elements, it is contemplated that any type of element or combination of different element types may be used to create an unstructured mesh of solid material 302.

In process 216, testing system 102 applies a simulated deformation corresponding to one or more of stress, strain, force, displacement and the like to the unstructured mesh of 3D image volume 128. In some embodiments of the invention, testing tool 130 is configured to execute one or more software programs 912 including an finite element (FE) solver to simulate the deformation conditions encountered by rock sample 104 in situ at its sub-surface location in the formation. As known in the art, FE analysis is used to solve complex problems by dividing the solution domain into smaller subregions or finite elements. In the context of an unstructured mesh, as mentioned above, a variety of element shapes and sizes are employed in the same solution domain. Each element is associated with a number of nodal points at which neighboring elements are connected to one another, generally with an interpolation function (commonly known as a shape function) representing the variation of the field variable over the element. A system of simultaneous algebraic equations for the overall system is typically formulated, based on physical arguments establishing equilibrium and compatibility at the nodal points. Boundary conditions are imposed on the edges of the solution domain by assigning specific nodal values of the dependent variables, or nodal loads/force. This system of equations is then solved for unknown nodal values such as stress, strain, force, and displacement. In this case, testing tool 130 is configured to include a FE solver, realized as the necessary logic, algorithms, etc., capable of performing this FE analysis in process 216 upon the unstructured mesh defined in process 214. The particular FE solver can be any type of conventional known FE solver, such as a linear direct solver, an iterative solver, an eigensolver, a nonlinear equation solver, or another FE solver.

Figure 3F:
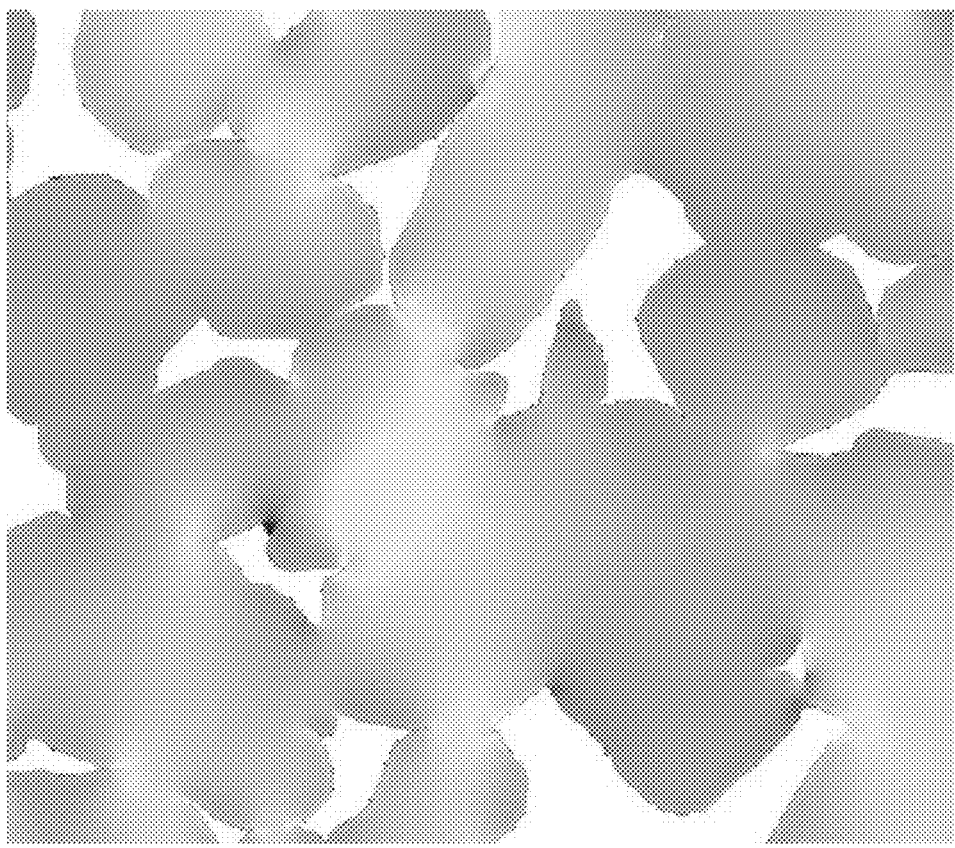
FIG. 3F is a digital plot illustrating the applied mesh of FIG. 3E under an example of simulated stress field and corresponding pore space deformation, according to embodiments of the invention.

In embodiments of the invention in which testing tool 130 utilizes finite element techniques to simulate a deformation applied to a volume of rock represented by digital image volume 128, process 216 is executed by computing device 120 subjecting the unstructured mesh of finite elements with labeled material properties to FE analysis to solve a system of elastic, viscoelastic, or other appropriate constitutive governing equations in light of boundary conditions that are assigned to the faces of the meshed volume, in a manner representative of the desired in situ sub-surface deformation conditions to be simulated. For example, these boundary conditions may take the form of applied displacements, in which case the FE solver calculates stress and strain for each finite element of the mesh volume. In other implementations, tractions (i.e. stresses) are applied to the unstructured mesh, in which case the FE solver calculates stress and strain for each finite element of the mesh volume. The magnitude and direction of the applied deformation preferably correspond to the desired in situ stress-strain condition, examples of which include hydrostatic, uniaxial, and triaxial stress-strain. In either case, testing tool 130 executes process 216 by numerically solving the appropriate governing equations (i.e., such as those for linear elasticity) across the volume represented by the unstructured mesh for the applied boundary conditions. From these stress-strain computations for linear elasticity, the FE solver can also calculate effective elastic properties (Young's modulus, Poisson's ratio, bulk modulus, and shear modulus, and the like) of the entire image volume 128. These elastic parameters are usually recovered by solving for the stiffness matrix, which relates stress to strain, or for the compliance matrix, which relates strain to stress. The effects of the simulated deformation affect the structure and attributes of the unstructured mesh. FIG. 3F illustrates an example of a simulated deformation where material stresses have been calculated on the mesh shown in FIG. 3E in response to an applied displacement boundary condition. As evident from a comparison of FIGS. 3E and 3F, this simulated deformation effects a compression of image volume 300 in the x-direction in this example.

In FIG. 3F, the elastic properties (E, v) of the solid matrix are assumed to be homogeneous throughout the volume, and are kept constant during the deformation stage. When clays or other significantly different elastic materials are present, it is useful to perform the simulations with elastic properties assigned to each mineral (quartz, clay, etc.). Moreover, when grain contacts are considered to have a significant impact on the overall mechanical behavior of the rock, such as with weakly consolidated sands, it is useful to take into account contact compliance/stiffness, which arises due to the presence of grain contacts. Usually, elastic properties that vary with applied stress/strain are assigned a stress dependent contact compliance (normal and tangential), using a variety of approaches, such as analytical models, experimental data, or heuristic functions. Analytical models for contact behavior (Hertz, Mindlin, Walton, Digby, etc.) usually assume that spherical grains are in contact and that the contact region is circular. These models can be applied within a simulation to adjust the elastic properties of the contact regions for each individual grain, taking into account each grains coordination number, which refers to the number of grain contacts for that grain. Moreover, as these models are usually functions of applied stress, the contact elastic properties can be adjusted as the deformation proceeds, depending upon the incremental stress or strains computed in the contact regions. As noted above, another approach to assigning elastic properties to the contact regions is to utilize experimental data, where dynamic elastic properties (compressional and shear wave velocities) measured as a function of stress are used to calibrate contact compliance, for example by assuming that the static elastic properties (Young's modulus, Poisson's ratio) of sample 128 to be equivalent to the dynamic elastic properties (Young's modulus, Poisson's ratio) extracted from the measured wave velocities.

Figure 4A:
FIGS. 4A through 4F are digital representations of a rock sample, to which an embodiment that involves the analysis of grain contact regions is applied.
Figure 4B:
Figure 4C:
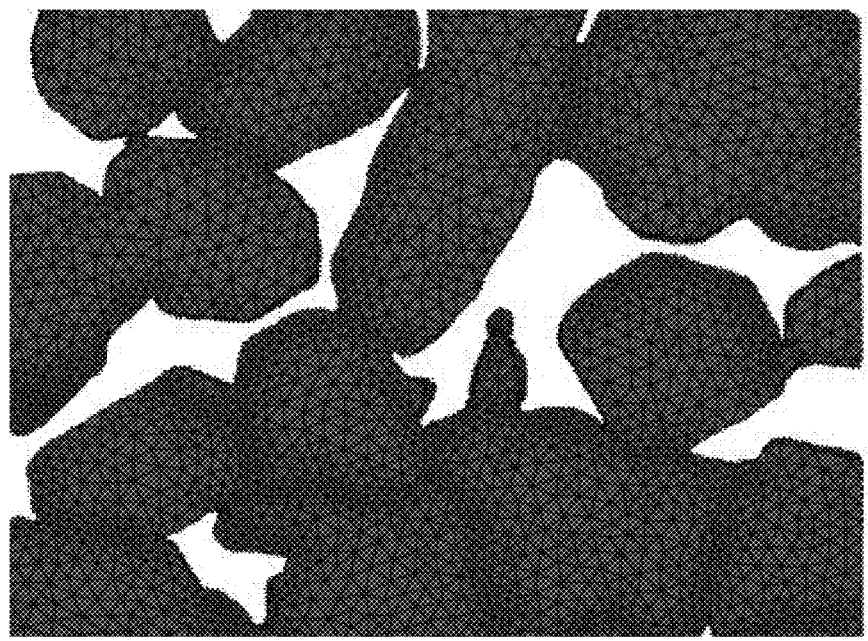

In order to take into account contact stiffness/compliance effects in the simulated deformation, it is necessary to perform optional process 212 in which grain and contact partitioning is applied to the segmented volume. FIGS. 4A and 4B illustrate an example of this grain and contact partitioning. In FIG. 4A, the solid matrix material is shown prior to partitioning process 212. FIG. 4B shows the same material following process 212, with the grain partitions shown by black values and the contacts between grans identified by light gray values. FIG. 4C shows the mesh created in process 214 for the grain-partitioned volume of FIG. 4B. In the example of FIG. 4C, refinement of the mesh in the vicinity of the contact regions is shown in FIG. 4C by the smaller triangles, relative to the larger triangle sizes in the interior of the solid grains. The desired stress/strain conditions are implemented numerically in smaller increments, with a series of deformations performed, to reach the desired in situ stress/strain condition. After each incremental deformation, a new grain and contact partition for the volume is typically created using process 212 on a voxelized representation of the deformed volume. Mesh refinement within the contact in this fashion is often useful because of the significant differences in the elastic properties between the contact regions and grain regions. This incremental mesh refinement approach, in which processes 212, 214, 216 are repeated, is illustrated in FIG. 2 by way of the dashed line. Alternatively, behavior in the contact region can be characterized by using suitably small mesh elements for both the interior of the solid grains and the contact regions, at a cost of increased computational requirements due to the larger number of elements in the model.

Figure 4D:
Figure 4E:
Figure 4F:
Figure 4G:
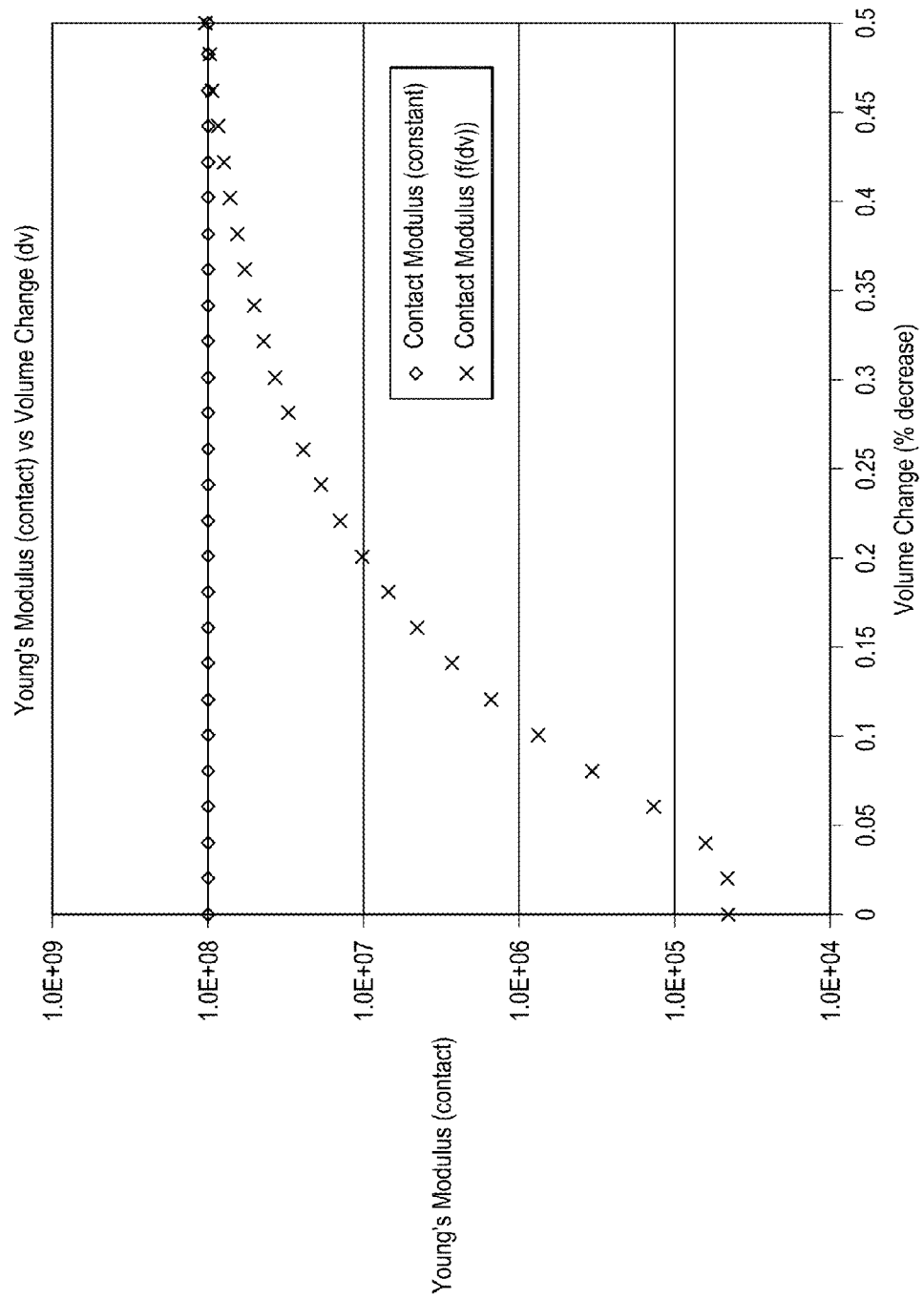
FIGS. 4G and 4H are plots illustrating the consideration of grain contact regions as described relative to the embodiment illustrated in FIGS. 4A through 4F.

As discussed above, the elastic properties of the contact regions can be modelled using analytical models, approximated from experiments, or postulated to behave according to heuristic functions. In FIG. 4G, two different functions are displayed for varying elastic properties of the contact regions as a function of displacement (expressed as percentage volume change in this example). The plot using the diamond symbols assumes that Young's modulus for the contact regions is less than the Young's modulus of the solid grains, and is constant with increasing deformation. The plot using the cross symbols assumes that Young's modulus of the contact regions varies non-linearly with increasing deformation. It is also possible to change the elastic properties of individual grains with deformation, if it is suspected that the grains contain compliant porosity below the image resolution. In FIGS. 4D through 4F, the normal strain is shown in the volume before deformation (FIG. 4D), after one incremental step in deformation without grain contact behavior (FIG. 4E), and with grain contact behavior assumed to vary according to a non-linear heuristic function (FIG. 4F). These FIGS. 4D through 4F illustrate clear differences in grain shape and pore space result from deformation that does include contact behavior, as compared with deformation not including contact behavior. In particular, more deformation in the volume appears when taking contact behavior into account, as evident by a reduction in porosity and by the change in grain shapes. FIG. 4F also shows that vastly different strains are induced in the contact regions relative to those within the grain regions. In particular, FIG. 4F shows that, after one increment in deformation, some grains are now in contact that were not prior to the incremental deformation, requiring grain partitioning process 212 to be repeated before subsequent deformations are performed.

Figure 4H:
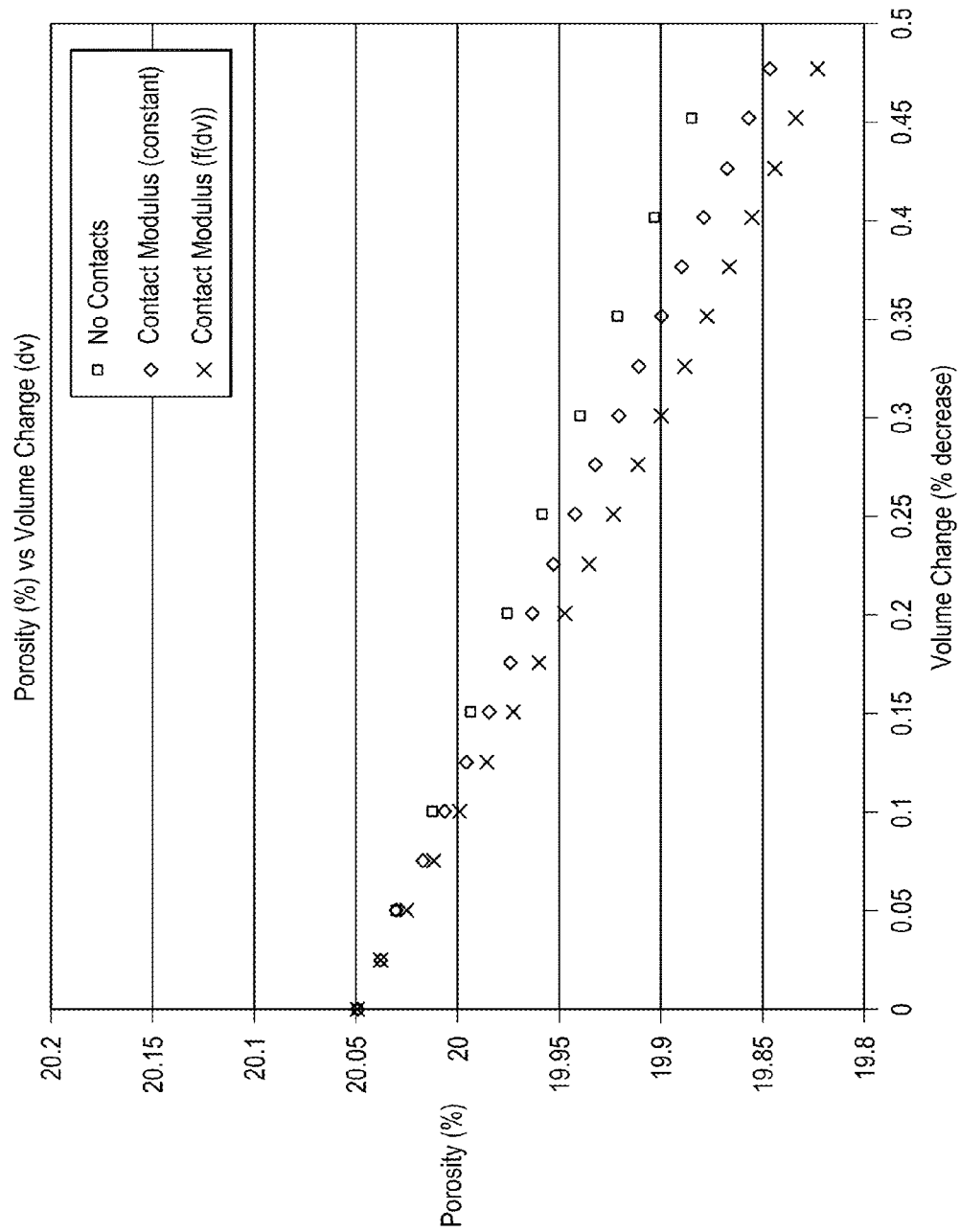

In FIG. 4H, porosity is plotted for three different deformation scenarios. The first assumption is that the elastic properties are homogeneous throughout the volume, with no contact behavior (FIG. 4E). The second assumption is that the heuristic function for contact behavior is constant with deformation, and the third assumption is that the heuristic function for contact behavior is non-linear with deformation (FIG. 4F), both of which are shown in FIG. 4G. As shown by these Figures, additional deformation is evident from the significant reductions in porosity that appear when taking contact behavior into account using the heuristic functions.

In process 220, testing tool 130 then performs digital numerical simulation to analyze one or more physical properties of rock sample 104 under the simulated in situ deformation conditions applied in process 216. It is contemplated that process 220 may be carried out by numerical analysis of the corresponding rock in the sub-surface under conditions represented by the final evolved stress state of the rock digital image volume 128. In the context of oil and gas exploration and production, petrophysical properties of interest such as porosity, formation factor, absolute and relative permeability, electrical properties (such as formation factor, cementation exponent, saturation exponent, tortuosity factor), capillary pressure properties (such as mercury capillary injection), elastic moduli and properties (such as bulk modulus, shear modulus, Young's modulus, Poisson's ratio, Lamé constants), and the like, may also be determined in process 220. These petrophysical properties may be estimated using an appropriate discretization of the deformed volume combined with appropriate numerical simulation, e.g. the direct numerical simulation of single phase fluid flow for computation of absolute permeability. The determination of some of these petrophysical properties in process 220 may also require numerical simulation using finite element methods, finite difference methods, finite volume methods, Lattice Boltzmann methods or any variety of other numerical approaches. As will be discussed in further detail below, relationships of different petrophysical properties of the material represented by image volume 128 with porosity, or relationships of other pairs of those properties, may also be estimated in process 220.

Figure 6:
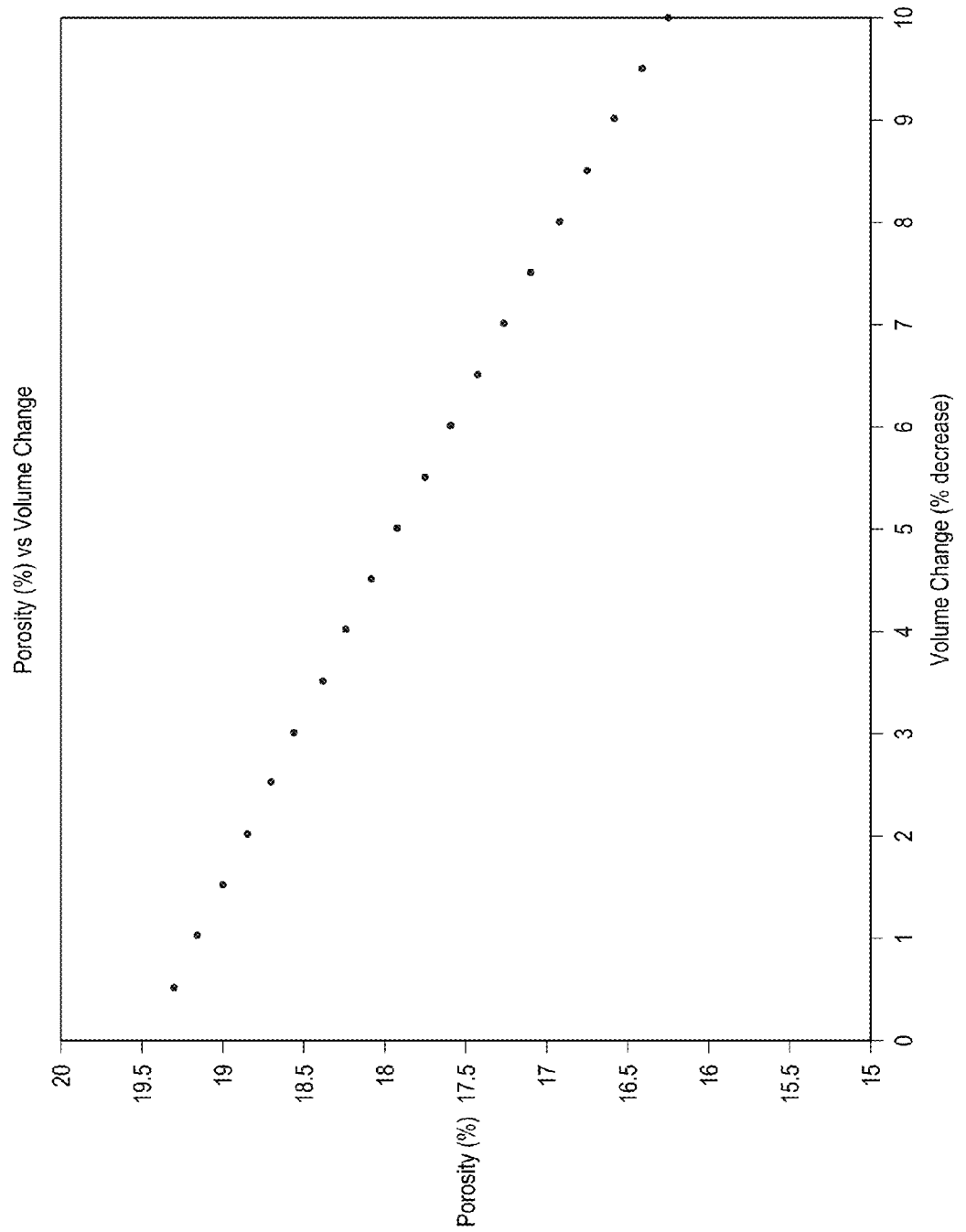
FIG. 6 is a plot of porosity of a rock sample versus volume change resulting from displacement applied in one direction, as determined by application of an embodiment of the invention.

In the process described above with reference to FIG. 2, testing system 102 has simulated the application of a deformation representing one subsurface condition. It is contemplated that testing system 102 may repeat this process for multiple simulated deformation conditions, including deformations of different amplitudes, directions, or types, in order to determine the petrophysical properties under different subsurface conditions, as well as to derive functions expressing the relationships of those properties to varying deformations. For example, FIG. 6 presents a graph of the calculated porosity for a given rock sample 104 under different simulated deformation conditions, in this example by plotting porosity as a function of displacement in the x-direction (i.e., compression, expressed as percentage volume change).

Referring now to FIGS. 5A through 5D, various detailed processes 220a through 220d by way of which process 220 may be carried out to determine physical properties of the rock formation from which rock sample 104 was acquired, under simulated conditions corresponding to the in situ deformation encountered in the sub-surface, will now be described. These approaches to determining physical properties are not mutually exclusive of one another, and as such one or more of these processes may be used in any given instance of process 220, depending on the particular properties to be characterized. It is further contemplated that those skilled in the art having reference to this specification will identify other similar techniques that may alternatively or additionally be used, such other alternatives being within the scope of the invention as hereinafter claimed.

FIG. 5A illustrates, in detail, process 220a by way of which porosity and other petrophysical properties of the sampled rock formation under the simulated deformation condition may be determined according to an embodiment of the invention. In process 410, testing tool 130 extracts the deformed volumetric mesh of the solid material of digital image volume 128 as produced by process 216, with the deformation resulting from the application of the simulated deformation conditions emulating the sub-surface environment, as described above. In process 412, testing tool 130 analyzes the full volume containing the deformed volumetric mesh to calculate the ratio of the volume of the solid phase to the total volume fraction (i.e., containing the solid material and deformed pore space). This ratio gives the volume fraction of the solid material, which can be utilized to determine the volume fraction of the pore space (known as porosity) through the simple relationship that the two fractions together add to unity. As illustrated in the example of FIG. 6, porosity decreases with increasing displacement due to the applied deformation. As such, it is contemplated that the porosity calculated in process 412 will be a good estimate of the porosity of the corresponding sub-surface rock formation from which rock sample 104 originated, as compared with porosity estimates based on analysis of images from rock samples at ambient surface conditions.

It is known in the art that certain petrophysical properties correlate to porosity. Examples of such porosity-correlated properties include permeability, formation factor. In process 414, testing tool 130 estimates one or more of these correlated properties from the porosity calculated in process 412, using rules of thumb that are established or otherwise known in the industry, or using correlations developed from laboratory experiments. The porosity value and any such correlated petrophysical properties are then stored in a memory resource of computing device 120 or a networked memory resource, as desired, for use in further analysis of the reservoir in the conventional manner.

FIG. 5B illustrates process 220b, according to which testing tool 130 in testing system 102 calculates certain petrophysical properties according to another embodiment of the invention. Process 220b begins with process 410, which as described above extracts the deformed volumetric mesh of the solid phase constituents of digital image volume 128 as produced by process 218, with the deformation resulting from the application of the simulated deformation conditions emulating the sub-surface environment, as described above.

In process 420, testing tool 130 operates to convert the deformed mesh geometry from process 410 into a voxelized geometry that is consistent with the input requirements of geometries used in a particular numerical analysis technique for determining the desired petrophysical properties. For example, the conversion of process 420 may voxelize the deformed unstructured mesh geometry into a structured grid or mesh form that is suitable for application to such algorithms as finite difference algorithms, Lattice Boltzmann algorithms, or both.

Figure 7:
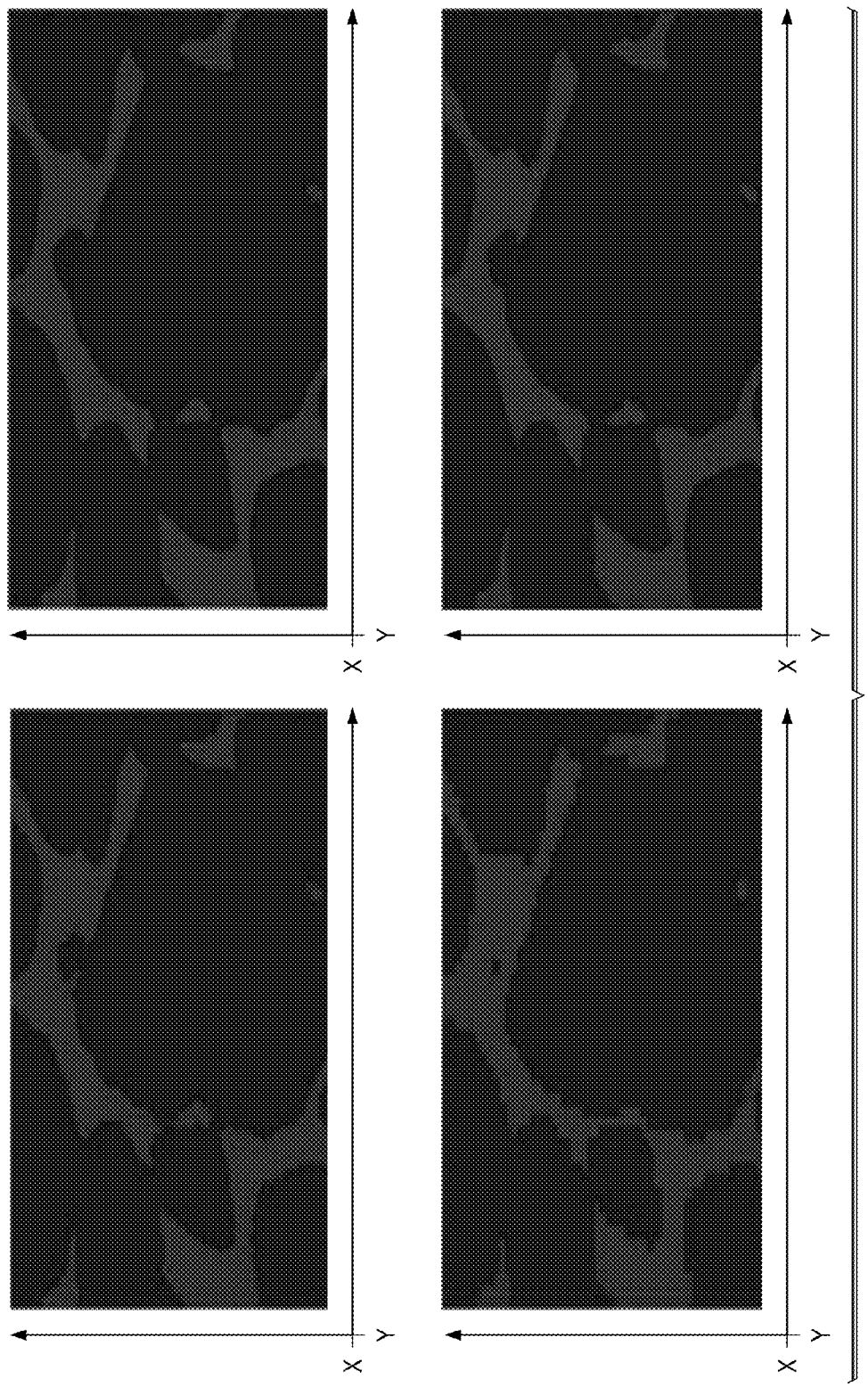
FIG. 7 is a comparison of cross-sectional views resulting from the conversion of the unstructured grid after deformation by a simulated stress to structured grids of varying resolution, according to an embodiment of the invention corresponding to FIG. 5B.

For example, computing device 120 may perform process 420 by converting the unstructured deformed mesh representing the solid material into a structured mesh representing the pore phase. Computing device 120 can then, also in conversion process 420, overlay a structured mesh onto the unstructured deformed mesh and extrapolate a point that exists at the center of each structured mesh block, followed by using a point detection algorithm to determine whether the center of each structured mesh block is inside or outside of the unstructured domain. Following this point detection, computing device 120 then determines whether a mesh block on the structured mesh should be identified as residing in the pore space or in the solid phase. FIG. 7 illustrates the result of this algorithm for one case of a deformed mesh, where the resolution of the overlaying structured grid dictates how well the structured grid represents the unstructured grid at different resolutions of the voxelization.

Figure 8:
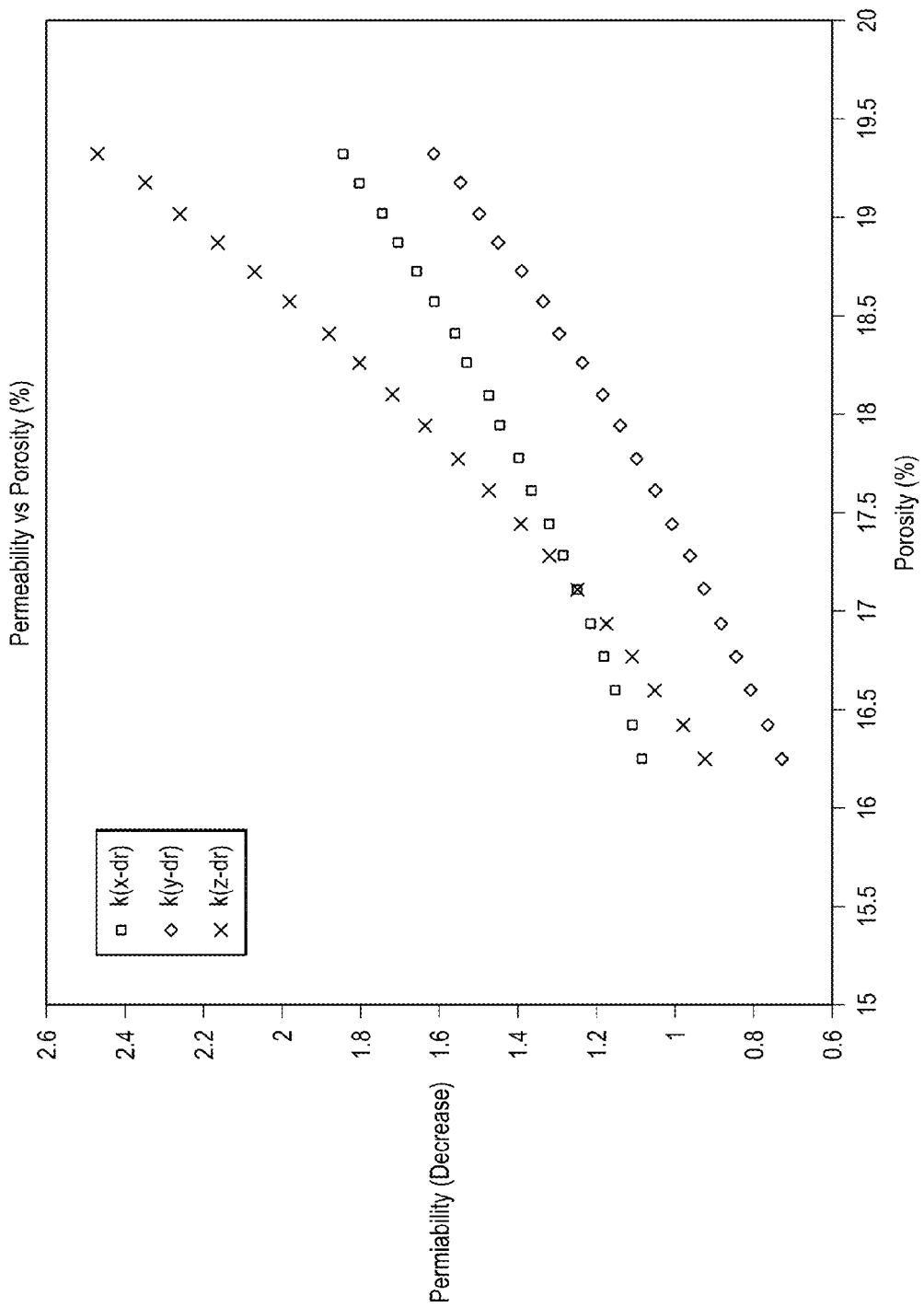
FIG. 8 is a plot of directional permeability of a rock sample versus porosity, as determined by application of an embodiment of the invention.

Following conversion process 420, testing tool 130 applies the desired numerical algorithm to compute the petrophysical properties, in process 422. For example, following the conversion into structured grids in process 420, computing device 120 (executing testing tool 130) may utilize existing Lattice-Boltzmann (LB) models to simulate single phase fluid flow in the pore space, from which properties such as permeability can be readily recovered. FIG. 8 illustrates the results of Lattice-Boltzmann simulation analysis for a set of geometries deformed by varying simulated deformation conditions, as resulting from linear elasticity computations in each of the primary flow directions (x, y, z). These results summarized in FIG. 8 support the expectation that permeability should decrease with the decreasing porosity resulting from uniaxial strain.

Figure 9:
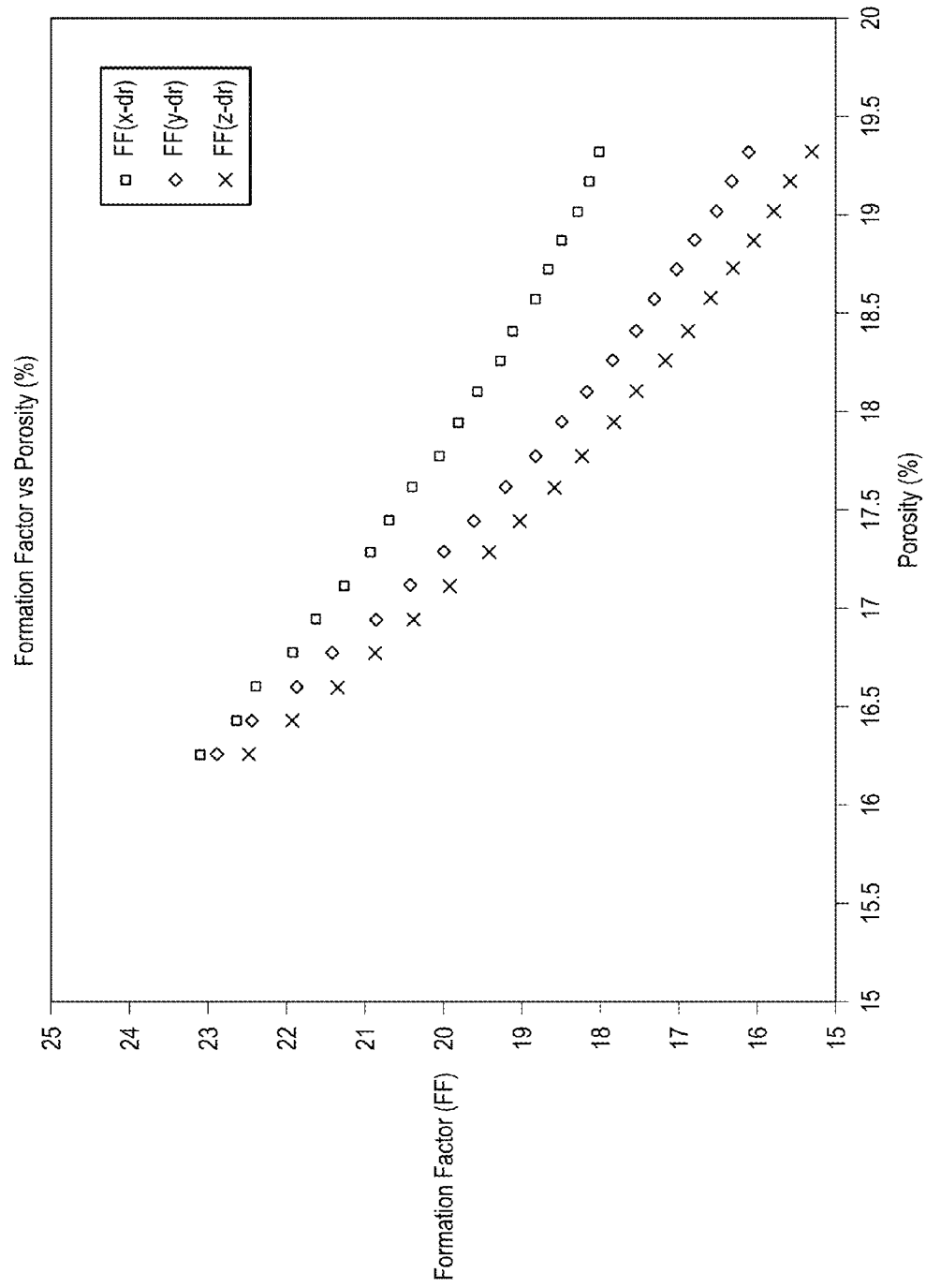
FIG. 9 is a plot of formation factor of a rock sample versus porosity, as determined by application of an embodiment of the invention.
Figure 10:
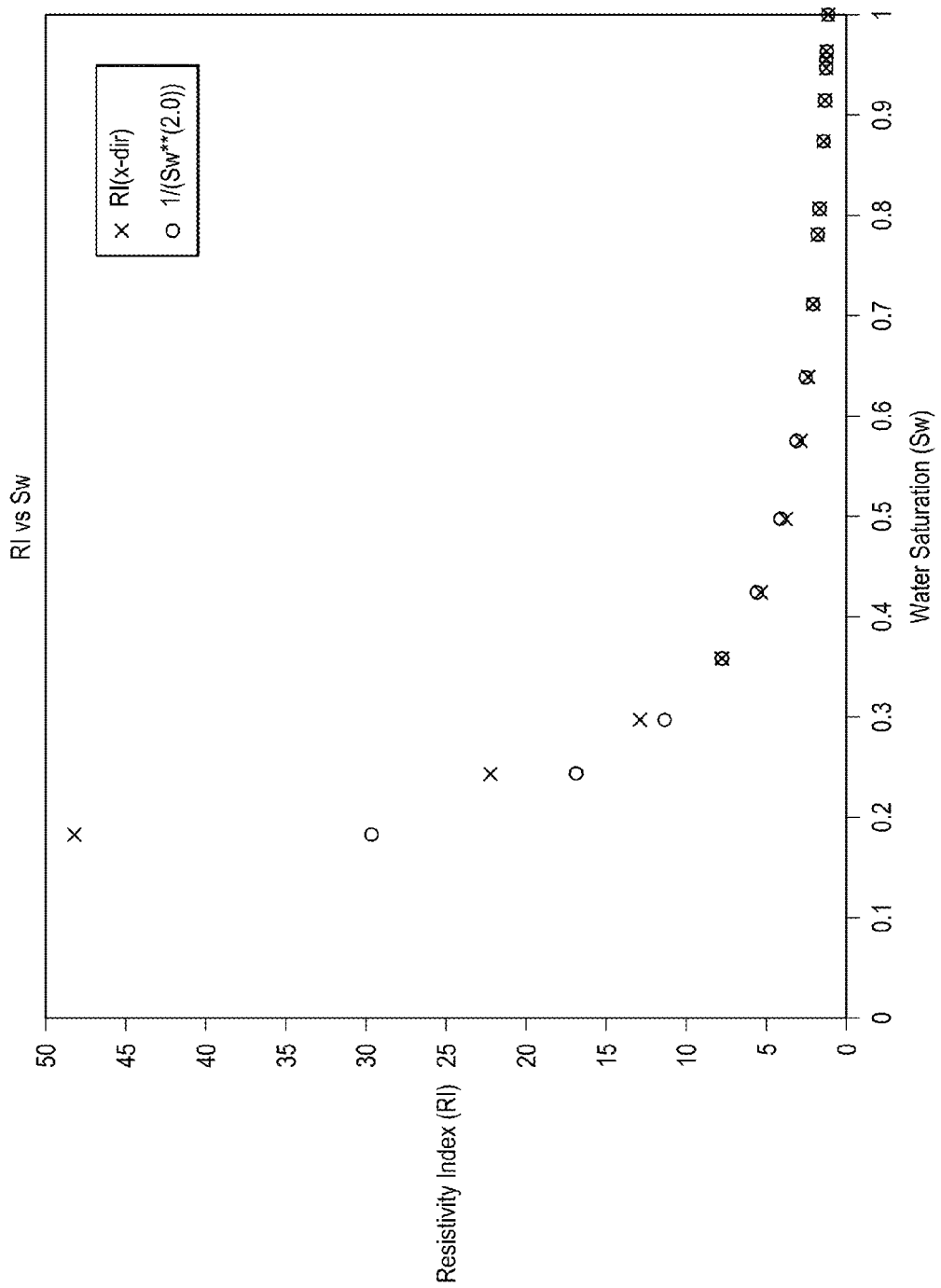
FIG. 10 is a plot of resistivity index of a rock sample versus water saturation, as determined by application of an embodiment of the invention.

Alternatively or in addition, process 422 may be used to calculate electrical properties using a structured mesh representing the deformed rock sample as generated in process 420. For example, a finite difference algorithm executed by computing device 120 can solve the Laplace equation for voltage distribution within the porous sample, from which the conductivity of the porous material can be recovered. Based on this conductivity analysis, computing device 120 can calculate such electrical properties as formation factor (FF) and resistivity index (RI), each of which is useful in the oil and gas exploration and production context. In the case of formation factor, the pore space is assumed to be entirely saturated with water, while in the case of resistivity index, oil and water are assumed to be distributed within the pore space. FIGS. 9 and 10 depict the dependence of FF and RI, respectively, with varying porosity at varying simulated deformation conditions. In these examples, a water wet scenario was considered where the distribution of oil and water at varying water saturation (SW) was based on a maximum inscribed sphere of the pore space.

As illustrated, both FF and RI increase with decreasing porosity. In FIG. 9, FF is calculated for all deformed geometries in each of the primary directions, while in FIG. 10, RI is shown only in the x-direction for the case of 5% total volume compression.

These electrical and other petrophysical properties as obtained from process 220b are then stored in a memory resource of computing device 120 or a networked memory resource, as desired, for use in further analysis of the reservoir in the conventional manner.

FIG. 5C illustrates process 220c, according to which testing tool 130 in testing system 102 calculates certain petrophysical properties according to another embodiment of the invention. As in the case of processes 220a, 220b, process 220c similarly begins with process 410, which as described above extracts the deformed volumetric mesh of the solid phase constituents of digital image volume 128 as produced by process 218, with the deformation resulting from the application of the simulated deformation conditions emulating the sub-surface environment, as described above.

In process 430 of process 220c, testing tool 130 identifies those elements of the deformed unstructured mesh that correspond to surface elements of the pore space, i.e. the pore "wall". The result of process 430 is a representation of the outer surfaces of the pore space of the portion of rock sample 104 represented by digital image volume 128, desirably in a form compatible with a conventional volume "meshing" software package. In process 432, testing tool 130 utilizes such a volume meshing package to construct or otherwise define a volumetric mesh of the pore space defined by the pore wall surface elements identified in process 430, desirably in a format suitable for analysis by an appropriate finite element analysis tool or other numerical tool, such as Lattice-Boltzmann. The volumetric mesh of the pore space generated in process 432 may be a structured mesh (i.e., a regular pattern of polygonal elements) or an unstructured mesh (i.e., an irregular pattern of polygonal elements with irregular connectivity), as desired.

Once the volumetric mesh of the pore space is generated in process 432, testing tool 130 then executes a finite element solver or other numerical algorithm in process 434 to compute the desired petrophysical properties based on that volumetric mesh of the pore space. One example of process 434 that may be carried out by computing device 120 and testing tool 130 is a computation of absolute permeability of rock sample 104 by modeling single phase fluid flow using a finite element solution of the Navier-Stokes equations, under boundary conditions that impose a pressure drop across the modeled volume. Other properties may also or alternatively be computed in process 434, using finite element solutions, or using other techniques such as finite difference, finite volume, Lattice-Boltzmann, network modeling, and the like to compute those properties as well as absolute permeability.

The petrophysical or other properties obtained from process 220c are then stored in a memory resource of computing device 120 or a networked memory resource, as desired, for use in further analysis of the reservoir in the conventional manner.

FIG. 5D illustrates process 220d, according to which testing tool 130 in testing system 102 calculates certain petrophysical or material properties using analytical models, according to another embodiment of the invention. Examples of properties that are contemplated to be recoverable by way of process 220d include those properties that are determined by or related to pore topology within the rock. As in the case of processes 220a through 220c described above, process 220d similarly begins with process 410, which as described above extracts the deformed volumetric mesh of the solid phase constituents of digital image volume 128 as produced by process 218, with the deformation resulting from the application of the simulated deformation conditions emulating the sub-surface environment, as described above.

In process 440, geometrical properties are extracted by testing tool 130 from the deformed volumetric mesh identified in process 410. Examples of these geometrical properties include measures such as surface-to-volume ratio of the grains or pores, the critical pore throat diameter recoverable from topological measures extracted from a deformed volumetric mesh of the pore space, as well as other structural parameters or model parameters identifiable from the deformed mesh. The particular format or data representing these geometrical properties extracted in process 440 should be compatible with one or more analytical models to be applied, in process 442, to determine or calculate the desired material property. In this process 442, testing tool 130 executes one or more particular analytical models capable of estimating the desired petrophysical property of interest from the extracted geometrical properties for the solid. Examples of these properties include flow properties and electrical properties, among others.

An example of a material and petrophysical property that may be determined by application of process 220d is the "tortuosity" of the material. As known in the art, the tortuosity of a porous material reflects the extent to which fluid paths through the material are twisted, or involve turns. For example, a material having a high number of closely-spaced sharp turns in its fluid paths of its pore space will exhibit a higher tortuosity than will a porous material in which the fluid paths are relatively straight. For the example of tortuosity, testing tool 130 may execute process 440 by representing the pore space by a population of maximum-sized inscribed spheres that fit within that pore space. A "streamline" is then defined in this process 440 by connecting the centroids of those inscribed spheres along each fluid path. Process 442 can then calculate tortuosity of the material by applying a measure such as the "arc-chord" ratio of the length of the curve represented by the centroid-to-centroid streamline to the distance between its ends (i.e., as the "crow flies").

Other tortuosity calculations known in the art may alternatively or additionally be applied by testing tool in process 442. For example, "rule of thumb" relationships may be used to determine properties such as absolute permeability according to the functional relationship of permeability to critical pore throat radius parameters extracted in process 440. Additionally, following the computation of one or more petrophysical properties in this manner, testing tool 130 may compute other properties of the material in process 442 based on those results. In any case, the petrophysical or other properties obtained from process 220d can then be stored in a memory resource of computing device 120 or a networked memory resource, as desired, for use in further analysis of the reservoir in the conventional manner.

Figure 2:
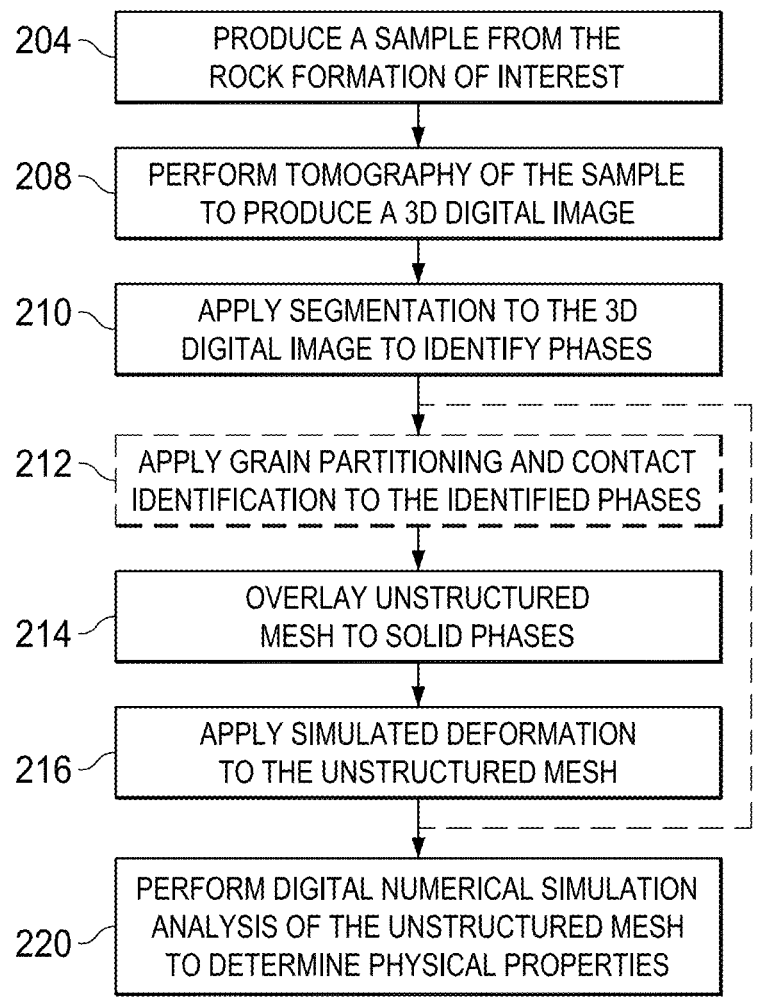
FIG. 2 is a flow diagram illustrating a method of operating a testing system in analyzing rock samples, according to embodiments of the invention.

As mentioned above, the particular detailed techniques 220a through 220d for performing process 220 in the overall method of FIG. 2 may be applied individually, or in some combination. It is further contemplated that those skilled in the art having reference to this specification will readily identify variations of these approaches, as well as alternative implementations and embodiments of the invention, and that such variations and alternatives are properly within the scope of the invention as claimed below.

As will also be evident to the skilled reader of this specification, these embodiments provide important benefits in the analysis of porous materials, such as samples of sub-surface formations at or near potential reservoirs of oil and gas. In particular, embodiments of this invention enable the use of direct numerical simulation techniques to analyze material properties, including petrophysical properties, of sub-surface formations under the deformation conditions applied to those formations in their sub-surface environment. This improves the ability of laboratory systems and analytical equipment to accurately characterize the sub-surface, over conventional direct numerical simulation techniques applied to image volumes acquired at surface ambient conditions. Furthermore, by simulating the in situ subsurface conditions of a rock sample using an image volume and additional numerical analysis according to embodiments of the invention, the time and cost for determining petrophysical properties can be reduced. Relative to laboratory measurements, which may take months to complete, the turnaround time for image based computation of stress/strain related petrophysical properties, can be reduced to days or less. Furthermore, by using a simulation approach to obtain estimates of subsurface properties under stress, it is possible to obtain many different evolved stress states from the one image of a rock volume, such an ensemble assisting an understanding the evolution of subsurface petrophysical properties during the development and production of reservoir rock. These and other advantages and benefits are contemplated to be made available by embodiments of the invention, as may be applicable to particular materials, situations, and implementations.

While this invention has been described according to its embodiments, it is of course contemplated that modifications of, and alternatives to, these embodiments, such modifications and alternatives obtaining the advantages and benefits of this invention, will be apparent to those of ordinary skill in the art having reference to this specification and its drawings. It is contemplated that such modifications and alternatives are within the scope of this invention as subsequently claimed herein.

What is claimed is:

1. A method of analyzing a rock sample, comprising the steps of:
    segmenting a digital image volume corresponding to one or more tomographic images of a rock sample, to associate voxels in the digital image volume with pore space or solid material;
    overlaying voxels corresponding to solid material in the segmented digital image volume with an unstructured finite element mesh;
    numerically simulating the application of a deformation to the unstructured mesh to produce a deformed volumetric mesh of the digital image volume under the simulated deformation; and
    then numerically analyzing a representation of the digital image volume corresponding to the deformed volumetric mesh to characterize a material property of the rock sample under conditions corresponding to the deformation.

2. The method of claim 1, further comprising:
    repeating the overlaying, simulating, and analyzing steps to characterize the material property over multiple deformation conditions.

3. The method of claim 1, wherein the deformation corresponds to one or more of a stress condition, a strain condition, a force condition, and a displacement condition.

4. The method of claim 1, further comprising:
    after the segmenting step, assigning values for elastic properties to voxels associated with solid material;
    wherein the numerically simulating step is performed using the assigned values for elastic properties.

5. The method of claim 1, further comprising:
    partitioning individual grains of solid material represented in the segmented digital image volume and identifying contact regions of those grains.

6. The method of claim 5, wherein the step of overlaying voxels with an unstructured finite element mesh overlays the contact regions with a finer pattern of finite elements than the finite elements applied to other portions of the partitioned grains.

7. The method of claim 6, further comprising:
    after the partitioning step, assigning values for elastic properties to voxels associated with solid material;
    wherein the values for elastic properties include values corresponding to contact compliance assigned to the identified contact regions;
    and wherein the numerically simulating step is performed using the assigned values for elastic properties.

8. The method of claim 7, further comprising:
    after a first instance of the numerically simulating step, repeating the partitioning, overlaying, and numerically simulating steps.

9. The method of claim 1, wherein the numerically simulating step comprises:
    defining boundary conditions corresponding to the deformation to be applied to a system of equations corresponding to constitutive equations of elasticity across the volume of solid material represented by the unstructured mesh; and
    executing a finite element solver to solve the system of equations for the defined boundary conditions for displacement of nodes of the unstructured mesh.

10. The method of claim 1, wherein the numerically analyzing step comprises:
    extracting a deformed volumetric mesh of the solid phase portion of the digital image volume;
    calculating porosity of a volume corresponding to the deformed volumetric mesh; and
    estimating one or more petrophysical properties according to a correlation of the petrophysical property to porosity.

11. The method of claim 1, wherein the numerically analyzing step comprises:
    extracting a deformed volumetric mesh of the solid phase portion of the digital image volume;
    converting the deformed volumetric mesh into a voxelized geometry representing a deformed volume representing pore space and solid material; and
    numerically computing one or more petrophysical properties from the deformed volumetric mesh.

12. The method of claim 11, wherein the converting step converts the deformed volumetric mesh into a voxelized geometry representing pore space in the volume;
    and wherein the numerically computing step comprises:
        simulating fluid flow in the pore space using a Lattice-Boltzmann model to determine permeability of the rock sample under the deformation.

13. The method of claim 11, wherein the numerically computing step comprises:
    solving a Laplace equation for voltage distribution within the volume, at an assumed water saturation level, to calculate either or both of a formation factor and resistivity index of the rock sample under the deformation.

14. The method of claim 1, wherein the numerically analyzing step comprises:
    extracting a deformed volumetric mesh of the solid phase portion of the digital image volume;
    identifying pore wall surface elements in the deformed volumetric mesh;
    generating a volumetric mesh of pore space based on the identified pore wall surface elements; and
    executing a numerical method to solve a system of equations applied to the volumetric mesh of the pore space to determine one or more petrophysical properties of the rock sample.

15. The method of claim 1, wherein the numerically analyzing step comprises:
    extracting a deformed volumetric mesh of the solid phase portion of the digital image volume;
    extracting geometrical properties from the deformed volumetric mesh;

applying the extracted geometrical properties to an analytical model to compute one or more petrophysical properties of the rock sample.

16. The method of claim 15, wherein the geometrical properties include a plurality of largest inscribed spheres fitting within the pore space represented by the deformed volumetric mesh;

and wherein the applying step comprises:
identifying one or more streamlines corresponding to line segments connecting centroids of the pore space; and
calculating tortuosity of the rock sample from the identified streamlines.

17. The method of claim 1, wherein the numerically analyzing step characterizes one or more material properties corresponding to one or more of a group of petrophysical properties consisting of absolute permeability, relative permeability, porosity, formation factor, cementation exponent, saturation exponent, tortuosity factor, bulk modulus, shear modulus, Young's modulus, Poisson's ratio, Lamé constants, and capillary pressure properties.

18. A system for analyzing material samples, the system comprising:
an imaging device configured to produce a digital image volume representative of a material sample; and
a computing device coupled to the imaging device and comprising:
one or more processors; and
one or more memory devices, coupled to the one or more processors, storing program instructions that, when executed by the one or more processors, cause the one or more processors to characterize, from a sample of a material, one or more material properties by performing a plurality of operations comprising:
segmenting a digital image volume corresponding to one or more tomographic images of a rock sample, to associate voxels in the digital image volume with pore space or solid material;
overlaying voxels corresponding to solid material in the segmented digital image volume with an unstructured finite element mesh;
numerically simulating the application of a deformation to the unstructured mesh to produce a deformed volumetric mesh of the digital image volume under the simulated deformation; and
then numerically analyzing a representation of the digital image volume corresponding to the deformed volumetric mesh to characterize a material property of the rock sample under conditions corresponding to the deformation.

19. The system of claim 18, wherein the imaging device comprises:
an X-ray computed tomography scanner.

20. The system of claim 18, wherein the plurality of operations further comprises:
repeating the overlaying, simulating, and analyzing operations to characterize the material property over multiple deformation conditions.

21. The system of claim 18, wherein the plurality of operations further comprises:
after the segmenting operation, assigning values for elastic properties to voxels associated with solid material;
wherein the numerically simulating operation is performed using the assigned values for elastic properties.

22. The system of claim 18, wherein the plurality of operations further comprises:
partitioning individual grains of solid material represented in the segmented digital image volume and identifying contact regions of those grains.

23. The system of claim 22, wherein the plurality of operations further comprises:
after the partitioning operation, assigning values for elastic properties to voxels associated with solid material;
wherein the operation of overlaying voxels with an unstructured finite element mesh overlays the contact regions with a finer pattern of finite elements than the finite elements applied to other portions of the partitioned grains;
wherein the values for elastic properties include values corresponding to contact compliance assigned to the identified contact regions;
and wherein the numerically simulating operation is performed using the assigned values for elastic properties.

24. A non-transitory computer readable storage medium storing program instructions that, when executed by one or more processors, cause the one or more processors to characterize, from a sample of a material, one or more material properties by performing a plurality of operations comprising:
segmenting a digital image volume corresponding to one or more tomographic images of a rock sample, to associate voxels in the digital image volume with pore space or solid material;
overlaying voxels corresponding to solid material in the segmented digital image volume with an unstructured finite element mesh;
numerically simulating the application of a deformation to the unstructured mesh to produce a deformed volumetric mesh of the digital image volume under the simulated deformation; and
then numerically analyzing a representation of the digital image volume corresponding to the deformed volumetric mesh to characterize a material property of the rock sample under conditions corresponding to the deformation.

25. The medium of claim 24, wherein the plurality of operations further comprises:
repeating the overlaying, simulating, and analyzing operations to characterize the material property over multiple deformation conditions.

26. The medium of claim 24, wherein the plurality of operations further comprises:
after the segmenting operation, assigning values for elastic properties to voxels associated with solid material;
wherein the numerically simulating operation is performed using the assigned values for elastic properties.

27. The medium of claim 24, wherein the plurality of operations further comprises:
partitioning individual grains of solid material represented in the segmented digital image volume and identifying contact regions of those grains.

28. The medium of claim 27, wherein the plurality of operations further comprises:
after the partitioning operation, assigning values for elastic properties to voxels associated with solid material;
wherein the operation of overlaying voxels with an unstructured finite element mesh overlays the contact regions with a finer pattern of finite elements than the finite elements applied to other portions of the partitioned grains;
wherein the values for elastic properties include values corresponding to contact compliance assigned to the identified contact regions;

and wherein the numerically simulating operation is performed using the assigned values for elastic properties.

* * * * *